United States Patent
Fendel et al.

(10) Patent No.: US 10,344,082 B2
(45) Date of Patent: Jul. 9, 2019

(54) ANTI-PARASITIC COMPLEXES

(71) Applicant: Fraunhofer-Gesellschaft zur Foerderung der angewandten Forschung e.V., Munich (DE)

(72) Inventors: Rolf Fendel, Aachen (DE); Stephanie Kapelski, Antwerp (BE); Stefan Barth, Cape Town (ZA); Rainer Fischer, Aachen (DE); Andreas Reimann, Krefeld (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

(21) Appl. No.: 15/507,173

(22) PCT Filed: Aug. 21, 2015

(86) PCT No.: PCT/EP2015/069247
§ 371 (c)(1),
(2) Date: Feb. 27, 2017

(87) PCT Pub. No.: WO2016/030292
PCT Pub. Date: Mar. 3, 2016

(65) Prior Publication Data
US 2017/0253650 A1    Sep. 7, 2017

(30) Foreign Application Priority Data

Aug. 26, 2014 (EP) .................................... 14182195

(51) Int. Cl.
*C12N 9/64* (2006.01)
*A61K 47/68* (2017.01)
*C07K 16/20* (2006.01)

(52) U.S. Cl.
CPC ........ *C07K 16/205* (2013.01); *A61K 47/6815* (2017.08); *A61K 47/6835* (2017.08); *C12N 9/6467* (2013.01); *C12Y 304/21079* (2013.01); *C07K 2317/24* (2013.01); *C07K 2317/622* (2013.01); *C07K 2317/76* (2013.01)

(58) Field of Classification Search
None
See application file for complete search history.

(56) References Cited

FOREIGN PATENT DOCUMENTS

| WO | 1993/004696 | 3/1993 |
| WO | 2008/011157 | 1/2008 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
de Silva et al (Malaria J., 10:266, 1-12, 2011).*
Hagemeyer et al. "Single-chain antibodies as diagnostic tools and therapeutic agents" Thrombosis and Haemostasis, Jun. 2009, 101(6):1012-1019.
Hehmann-Titt et al. "Improving the therapeutic potential of human granzyme B for targeted cancer therapy." Antibodies, Jan. 16, 2013, 2(1):19-49.
Kariu et al. "CelTOS, a novel malarial protein that mediates transmission to mosquito and vertebrate hosts." Molecular Microbiology, Mar. 20, 2006, 59(5):1369-1379.
Surolia, Namita. "Receptor-mediated targeting of toxins to intraerythrocytic parasite Plasmodium falciparum." Advanced Drug Delivery Reviews, Mar. 1, 2000, 41(2):163-170.
Yoshida et al. "Bacteria expressing single-chain immunotoxin inhibit malaria parasite development in mosquitoes." Molecular and Biochemical Parasitology, Mar. 1, 2001, 113(1):89-96, Elsevier Science Publishers, Amsterdam, NL.
PCT/EP2015/069247 International Search Report dated Jan. 20, 2016.

* cited by examiner

*Primary Examiner* — Brian Gangle
(74) *Attorney, Agent, or Firm* — Wagenknecht IP Law Group PC

(57) ABSTRACT

The technology provided herein relates to novel anti-parasitic complexes, in particular recombinant fusion proteins suitable as human and/or animal drugs against a parasite of the phylum Apicomplexa, in particular against *Plasmodium falciparum* (*P. falciparum*) comprising at least one component A and at least one component B, characterized in that component A has a binding activity for cellular surface structures presented on the surface of a parasite of the phylum Apicomplexa or for parasitic antigens presented on a parasitized host cell, and component B is a compound having anti-parasitic activity.

14 Claims, 11 Drawing Sheets

Specification includes a Sequence Listing.

Figure 2

| Species | Definitive host | Intermediate host | Preferred host environment |
|---|---|---|---|
| Plasmodium falciparum | Mosquito | Human | Erythrocyte (red blood cell) |
| Plasmodium vivax | Mosquito | Human | Erythrocyte |
| Plasmodium berghei | Mosquito | Rat | Erythrocyte |
| Plasmodium yoelii | Mosquito | Rat | Erythrocyte |
| Theileria annulata | Tick | Bovine | Leukocyte (white blood cell) |
| Theileria parva | Tick | Bovine | Leukocyte |
| Eimeria tenella | Poultry | None | Intestinal tract |
| Sarcocystis falcatula | Opossum | Avian | Leukocyte |
| Sarcocystis neurona | Opossum | Equine | Leukocyte |
| Toxoplasma gondii | Feline | Warm-blooded animals | Broad range |
| Neospora hughesi | Unknown | Equine | Broad range |
| Neospora caninum | Dogs | Bovine/Equine/Ovine | Broad range |
| Gregarina niphandrodes | Arthropods, nematodes and annelids | None | Intestinal track |
| Cryptosporidium hominis | Human | None | Intestinal track |
| Cryptosporidium parvum | Mammal | None | Intestinal track |

Figure 4

SRHIDDDDK IIGGHEAKPHSRPYMAFLMIWDQKSLKRCGGFLIRDDFVLTAAHCWGSSINVTLGAHNI
rEK-cleavage site          Granzyme B KEQEPTQQFIPVKRAIPHPAYNPKNFSNDIMLLQLERKAKRTRAVQPLRLPSNKAQVKPGQTCSVAGWG
                 ...Granzyme B...

QTAPLGKHSHTLQEVKMTVQEDRKCESDLRHYYDSTIELCVGDPEIKKTSFKGDSGGPLVCNKVAQGIVS
                 ...Granzyme B...

YGKNNGMPPRACTKVSSFVHWIKKTMKRY AEHEGDAAQPAMA DVQLQESGPGLVKPSQSLSLTC
      ...Granzyme B...                              linker              VH TVTGYSITSDFAWNWIRQFPGNRLEWMGYMGYTGSTSYNPSLRGRISITRDTSKNQFFLQLNSVTTEDT
                 ...VH...

ATYYCARGDYYGSRGYFDVWGAGTTVTVSS GGGGSGGGGSSGGGSGGGGS EIVLTQSPALMAASP
      ...VH...                            linker                        VL GEKVTITCSVSSSIRSSNLHWYQQKSDTSPKPWIYGTSNLASGVPVRFSGSGSGTSYSLTISTMEAEDAATY
                 ...VL...

YCQQWSSYPFTFGSGTKLEIK AAANSSLGSGWSHPQFEKTGHHHHHHHHGGQ
      ...VL...                    Streptavidin- and HIS-tag

Figure 8

A) Amino acid sequence of human wild type granzyme B (SEQ ID NO: 2)

```
1     iigghvakph srpymaylmi wdqkslkrcg gflirddfvl taahcwgssi nvtlgahnik
61    eqeptqqfip vkraiphpay npknfsndim llqlerkakr travqplrlp snkaqvkpgq
121   tcsvagwgqt aplgkhshtl qevkmtvqed rkcesdlrhy ydstielcvg dpeikktsfk
181   gdsggplvcn kvaqgivsyg rnngmpprac tkvssfvhwi kktmkry
```

B) Nucleic acid sequence of wild type human granzyme B (SEQ ID NO: 3)

```
atcatcgggg gacatgaggc caagccccac tcccgcccct acatggcttt tcttatgatc    60
tgggatcaga agtctctgaa gaggtgcggt ggcttcctga tacgagacga cttcgtgctg   120
acagctgctc actgttgggg aagctccata aatgtcacct gggggccca caatatcaag    180
gaacaggagc cgacccagca gtttatccct gtgaaaagag ccatccccca tccagcctat   240
aatcctaaga acttctccaa tgacatcatg ctactgcagc tggagagaaa ggccaagcgg   300
accagagctg tgcagcccct caggctacct agcaacaagg cccaggtgaa gccagggcag   360
acatgcagtg tggccggctg ggggcagacg gccccctgg gaaaacactc acacacacta    420
caagaggtga agatgacagt gcaggaagat cgaaagtgcg aatctgactt acgccattat   480
tacgacagta ccattgagtt gtgcgtgggg gacccagaga ttaaaaagac ttcctttaag   540
ggggactctg gaggccctct tgtgtgtaac aaggtggccc agggcattgt ctcctatgga   600
cgaaacaatg gcatgcctcc acgagcctgc accaaagtct caagctttgt acactggata   660
aagaaaacca tgaaacgcta c                                              681
```

Figure 9

Nucleic acid sequences of serpin B9 resistant granzyme B variants

A) Variant Gb R28K (SEQ ID NO: 4)

```
atcatcgggg gacatgaggc caagccccac tcccgcccct acatggcttt tcttatgatc    60
tgggatcaga agtctctgaa gaagtgcggt ggcttcctga tacgagacga cttcgtgctg   120
acagctgctc actgttgggg aagctccata aatgtcacct gggggccca caatatcaag    180
gaacaggagc cgacccagca gtttatccct gtgaaaagag ccatccccca tccagcctat   240
aatcctaaga acttctccaa tgacatcatg ctactgcagc tggagagaaa ggccaagcgg   300
accagagctg tgcagcccct caggctacct agcaacaagg cccaggtgaa gccagggcag   360
acatgcagtg tggccggctg ggggcagacg gccccctgg gaaaacactc acacacacta    420
caagaggtga agatgacagt gcaggaagat cgaaagtgcg aatctgactt acgccattat   480
tacgacagta ccattgagtt gtgcgtgggg gacccagaga ttaaaaagac ttcctttaag   540
gggactctg gaggccctct tgtgtgtaac aaggtggccc agggcattgt ctcctatgga    600
cgaaacaatg gcatgcctcc acgagcctgc accaaagtct caagctttgt acactggata   660
aagaaaacca tgaaacgcta c                                             681
```

B) Variant Gb R201A (SEQ ID NO: 5)

```
atcatcgggg gacatgaggc caagccccac tcccgcccct acatggcttt tcttatgatc    60
tgggatcaga agtctctgaa gaggtgcggt ggcttcctga tacgagacga cttcgtgctg   120
acagctgctc actgttgggg aagctccata aatgtcacct gggggccca caatatcaag    180
gaacaggagc cgacccagca gtttatccct gtgaaaagag ccatccccca tccagcctat   240
aatcctaaga acttctccaa tgacatcatg ctactgcagc tggagagaaa ggccaagcgg   300
accagagctg tgcagcccct caggctacct agcaacaagg cccaggtgaa gccagggcag   360
acatgcagtg tggccggctg ggggcagacg gccccctgg gaaaacactc acacacacta    420
caagaggtga agatgacagt gcaggaagat cgaaagtgcg aatctgactt acgccattat   480
tacgacagta ccattgagtt gtgcgtgggg gacccagaga ttaaaaagac ttcctttaag   540
gggactctg gaggccctct tgtgtgtaac aaggtggccc agggcattgt ctcctatgga    600
gcaaacaatg gcatgcctcc acgagcctgc accaaagtct caagctttgt acactggata   660
aagaaaacca tgaaacgcta c                                             681
```

Figure 10

Nucleic acid sequence of a further serpin B9 resistant granzyme B variant

A) Variant Gb R201K (SEQ ID NO: 6)

```
atcatcgggg gacatgaggc caagccccac tcccgcccct acatggcttt tcttatgatc    60
tgggatcaga agtctctgaa gaggtgcggt ggcttcctga tacgagacga cttcgtgctg   120
acagctgctc actgttgggg aagctccata aatgtcacct tggggggccca caatatcaag   180
gaacaggagc cgacccagca gtttatccct gtgaaaagag ccatccccca tccagcctat   240
aatcctaaga acttctccaa tgacatcatg ctactgcagc tggagagaaa ggccaagcgg   300
accagagctg tgcagcccct caggctacct agcaacaagg cccaggtgaa gccagggcag   360
acatgcagtg tggccggctg ggggcagacg gccccctgg gaaaacactc acacacacta   420
caagaggtga agatgacagt gcaggaagat cgaaagtgcg aatctgactt acgccattat   480
tacgacagta ccattgagtt gtgcgtgggg gacccagaga ttaaaaagac ttcctttaag   540
ggggactctg gaggccctct tgtgtgtaac aaggtggccc agggcattgt ctcctatgga   600
aagaacaatg gcatgcctcc acgagcctgc accaaagtct caagctttgt acactggata   660
aagaaaacca tgaaacgcta c                                             681
```

Figure 11

Amino acid sequences of further serpin B9 resistant granzyme B variants

A) Variant with the substitution R28A (Gb R28A) (SEQ ID NO:7)

```
1        iigghvakph srpymaylmi wdqkslkacg gflirddfvl taahcwgssi nvtlgahnik
61       eqeptqqfip vkraiphpay npknfsndim llqlerkakr travqplrlp snkaqvkpgq
121      tcsvagwgqt aplgkhshtl qevkmtvqed rkcesdlrhy ydstielcvg dpeikktsfk
181      gdsggplvcn kvaqgivsyg rnngmpprac tkvssfvhwi kktmkry
```

B) Variant with the substitution R28K (Gb R28K) (SEQ ID NO:8)

```
1        iigghvakph srpymaylmi wdqkslkkcg gflirddfvl taahcwgssi nvtlgahnik
61       eqeptqqfip vkraiphpay npknfsndim llqlerkakr travqplrlp snkaqvkpgq
121      tcsvagwgqt aplgkhshtl qevkmtvqed rkcesdlrhy ydstielcvg dpeikktsfk
181      gdsggplvcn kvaqgivsyg rnngmpprac tkvssfvhwi kktmkry
```

C) Variant with the substitution R201A (Gb R201A) (SEQ ID NO:9)

```
1        iigghvakph srpymaylmi wdqkslkrcg gflirddfvl taahcwgssi nvtlgahnik
61       eqeptqqfip vkraiphpay npknfsndim llqlerkakr travqplrlp snkaqvkpgq
121      tcsvagwgqt aplgkhshtl qevkmtvqed rkcesdlrhy ydstielcvg dpeikktsfk
181      gdsggplvcn kvaqgivsyg anngmpprac tkvssfvhwi kktmkry
```

D) Variant with the substitution R201K (Gb R201K) (SEQ ID NO:10)

```
1        iigghvakph srpymaylmi wdqkslkrcg gflirddfvl taahcwgssi nvtlgahnik
61       eqeptqqfip vkraiphpay npknfsndim llqlerkakr travqplrlp snkaqvkpgq
121      tcsvagwgqt aplgkhshtl qevkmtvqed rkcesdlrhy ydstielcvg dpeikktsfk
181      gdsggplvcn kvaqgivsyg knngmpprac tkvssfvhwi kktmkry
```

ANTI-PARASITIC COMPLEXES

CROSS REFERENCE TO RELATED APPLICATIONS

This is a national phase application of international patent application no. PCT/EP2015/069247, filed on Aug. 21, 2015, which itself claims priority to European application EP 14182195.9, filed Aug. 26, 2014. All of the applications referred to in this paragraph are incorporated by reference in their entireties herein.

REFERENCE TO SEQUENCE LISTING SUBMITTED ELECTRONICALLY

The official copy of the sequence listing is submitted electronically via EFS-Web as an ASCII formatted sequence listing with file "PCTEP2015069247_2017_12_SEQID" created on Dec. 11, 2017, filed on Jan. 31, 2018 and having a size of 20 Kilobytes. The sequence listing contained in this ASCII formatted document forms part of the specification and is herein incorporated by reference in its entirety.

FIELD OF THE DISCLOSURE

The technology provided herein relates to novel anti-parasitic complexes, in particular recombinant fusion proteins suitable as human and/or animal drugs against a parasite of the phylum Apicomplexa, in particular against *Plasmodium falciparum* (*P. falciparum*) comprising at least one component A and at least one component B, characterized in that component A has a binding activity for cellular surface structures presented on the surface of a parasite of the phylum Apicomplexa or for parasitic antigens presented on a parasitized host cell, and component B is a compound having anti-parasitic activity.

Nucleic acid molecules encoding said fusion protein and complexes, vectors, host cells containing the nucleic acids and methods for preparation and producing such complexes; compositions and methods for using said complexes for the treatment of diseases, in particular of malaria are also encompassed by the present disclosure.

BACKGROUND

The Apicomplexa are an eukaryotic protozoan phylum of around 5000 species including parasites which belong to the most successful and devastating pathogens today, infecting a wide range of animals from mollusks to mammals. Many species of Apicomplexa cause diseases of medical and veterinary importance and represent a significant economic burden and global healthcare challenge. Members of the phylum include:

- *Plasmodium*, the etiological agent of malaria, afflicting 10-40% of world population and accounting for one-in-five deaths among children under the age of five in Africa
- *Toxoplasma gondii*, the causative agent of toxoplasmosis. From one-third to half of the world's human population is estimated to carry a *Toxoplasma* infection. It is a major pathogen to humans with a weakened immune system, such as AIDS patients or pregnant women
- *Cryptosporidium*, a waterborne pathogen which typically does not cause serious illness in healthy people, but is a big health problem for immuno-compromised people, and

- the agricultural parasites *Eimeria* (infects poultry and causes annual losses in revenue totaling nearly a billion dollars), *Neospora* (an important pathogen in cattle and dogs),
- *Babesia* (thought to be the second most common blood parasites of mammals with a major health impact on domestic animals) and *Theileria* (causative agent of theileriosis a disease of cattle, sheep and goats).

The apicomplexan life cycle is complex and can be divided into three main stages wherein the first two serve for the asexual replication of the pathogen (more precise of the invasive stages of these protists called sporozoites and merozoites) and the third stage defines the sexual reproduction of the parasite. While the general life cycle is common to the Apicomplexa phylum, there are striking differences between species.

FIG. 1 shows the apicomplexan life cycles. As mentioned above, the members of Apicomplexa share a generalized life cycle, even though each species has its own specializations. *Plasmodium* spp. and *Theileria* spp. are transmitted and undergo sexual recombination in an insect vector, the *Anopheles* mosquito and *Rhipicephalus* tick, respectively. *Cryptosporidium* is able to autoinfect its host; the oocyst can sporulate and excyst in the same host, maintaining the infection for months to years. The Coccidian parasites are represented in this figure by *Toxoplasma*, which is able to infect the majority of warm-blooded animals. The differentiation of *Toxoplasma tachyzoites* into gametocytes is triggered only when members of the cat family (Felidae) are infected (Wasmuth, Daub et al. 2009).

Some Apicomplexa require a single host (e.g. *Cryptosporidium*), whereas others are more complex, requiring sexual reproduction in the vector species for transmission (e.g. *Theileria* and *Plasmodium*; see FIG. 2).

Although members of the Apicomplexa infect different host and cell types, they have a similar number of defining organelles involved in host cell attachment, invasion, and the establishment of an intracellular parasitophorous vacuole within the host cell. The arsenal of organelles varies between species, but typically includes rhoptries, micronemes, and dense granules. To develop novel anti-parasitic compounds and increase the understanding of apicomplexan biology, several large-scale-sequencing projects were initiated and the availability of genomic data sets for 15 species opened the way for the identification of conserved protein families and their functions within the phylum and in the above-mentioned processes. Domain analysis also identified both the taxonomic distribution of apicomplexan domains as well as domain architectures specific to the Apicomplexa.

In contrast to bacterial pathogens, these apicomplexan parasites are eukaryotic and share many metabolic pathways with their animal hosts. This fact makes therapeutic target development extremely difficult—a drug that harms an apicomplexan parasite is also likely to harm its human host.

Malaria is a disease caused by infection with parasites of the phylum Apicomplexa protozoan, namely parasites of the genus *Plasmodium*, globally causing more than 200 million new infections and 700 thousand deaths every year. Malaria is especially a serious problem in Africa, where one in every five (20%) childhood deaths is due to the effects of the disease. An African child has on average between 1.6 and 5.4 episodes of malaria fever each year.

Malarial diseases in humans are caused by five species of the *Plasmodium* parasite: *P. falciparum, P. vivax, P. ovale, P. malariae* and *P. knowlesi*, wherein the most prevalent being *P. falciparum* and *Plasmodium vivax*. Malaria caused by *P.*

*falciparum* (also called malignantor malaria, *falciparum* malaria or malaria *tropica*) is the most dangerous form of malaria, with the highest rates of complications and mortality. Almost all malarial deaths are caused by *P. falciparum*.

Briefly, the plasmodial life cycle in man starts with the inoculation of a few sporozoites through the bite of an *Anopheles* mosquito. Within minutes, sporozoites invade the hepatocyte and start their development, multiplying by schizogony. In the case of *P. vivax* and *P. ovale*, some sporozoites may differentiate into hypnozoites, responsible for late relapses of the infection. After a period of 5-14 days—depending on the plasmodial species—schizonts develop into thousands of merozoites that are freed into the bloodstream and invade the red blood cells (RBCs). In the RBC, each merozoite develops into a trophozoite that matures and divides, generating a schizont that, after fully matured, gives rise to up to 32 merozoites within 42-72 h, depending on the plasmodial species. The merozoites, released into the bloodstream, will invade other RBC, maintaining the cycle. Some merozoites, after invading a RBC, develop into sexual forms—the male or female gametocytes which also enter the bloodstream after maturation and erythrocyte rupture. When a female *Anopheles* mosquito takes its blood meal and ingests the gametocytes, it will become infected. In the mosquito gut, the male gametocyte fuses with the female gametocyte, forming the ookinete, which binds to and passes through the gut wall, remains attached to its external face and transforms into the oocyst. The oocyst will divide by sporogony, giving rise to thousands of sporozoites that are released in the body cavity of the mosquito and eventually migrate to its salivary gland, where they will maturate, becoming capable of starting a new infection in humans when the mosquito bites the host for a blood meal.

Resistance of *P. falciparum* to the existing anti-malarial drug chloroquine emerged in the sixties and has been spreading since then. In addition, the malaria parasite has developed resistance to most other anti-malarial drugs over the past decades. This poses a major threat to public health in tropical countries and to travellers. There is every reason to believe that the prevalence and degree of anti-malarial drug resistance will continue to increase.

Therefore the availability of novel therapeutic strategies against malaria would be highly advantageous.

SUMMARY OF THE INVENTION

The present disclosure relates to novel anti-parasitic complexes, in particular recombinant fusion proteins suitable as human and/or animal drugs against a parasite of the phylum Apicomplexa, in particular against *P. falciparum* comprising at least one component A and at least one component B, characterized in that component A has a binding activity for cellular surface structures presented on the surface of a parasite of the phylum Apicomplexa or for parasitic antigens presented on a parasitized host cell, and component B is a compound, in particular a polypeptide having anti-parasitic activity.

The present disclosure relates to novel isolated complexes, in particular to isolated recombinant fusion proteins for preventing, and/or treating of malaria.

In a first aspect, embodiments of the disclosure relate to isolated complexes comprising at least one component A and at least one component B, characterized in that component A has a binding activity for cellular surface structures presented on the surface of a parasite of the phylum Apicomplexa, and component B is a compound having anti-parasitic activity.

In particular, embodiments of the disclosure relate to isolated complexes comprising at least one component A and at least one component B, characterized in that component A has a binding activity either for cellular surface structures presented on the surface of a parasite of the phylum Apicomplexa, in particular *P. falciparum* or for parasitic antigens presented on a parasitized host cell and component B is a compound having anti-parasitic activity, wherein the compound having anti-parasitic activity is wild type human granzyme B or a variant or a functional fragment thereof.

In still another aspect, embodiments of this disclosure provide nucleic acids encoding said complexes, in particular said isolated fusion proteins as well as vectors and host cells comprising such nucleic acids.

In other aspects, this disclosure relates to compositions comprising a complex, in particular an isolated recombinant fusion protein as described herein, wherein the compositions may be useful for, or used in therapeutic applications. In one advantageous embodiment, the composition is used as a therapeutically composition for the treatment of malaria, in particular of malaria *tropica*.

In a further aspect, embodiments of this disclosure relate to methods for producing said complexes as recombinant fusion proteins in a host cell by transforming the host cell with a DNA construct, advantageously including a promoter having transcriptional activity in the host cell, cultivating the transformed host cell in a suitable culture medium to allow expression of said fusion proteins and producing the fusion proteins. The method may also include recovering or isolating the produced fusion proteins.

In a further aspect, the disclosure relates to purified complexes, in particular to recombinant fusion proteins comprising an antibody or an antigen-binding portion thereof as a specific binding domain for cellular surface structures presented on the surface of a parasite of the phylum Apicomplexa (component A) and an effector domain having anti-parasitic activity (component B); medicaments comprising such a complex in combination with a pharmacologically acceptable carrier or diluent and the use of such a complex for treating malaria, in particular malaria *tropica*.

Further aspects relates to the use of a complex according to the present disclosure for the treatment of malaria, in particular malaria *tropica*.

Further aspects relates to methods for treating malaria comprising: administering to a subject in need thereof a complex according to the present disclosure.

Before the disclosure is described in detail, it is to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is moreover to be understood that, in case parameter ranges are given which are delimited by numeric values, the ranges are deemed to include these limitation values.

BRIEF DESCRIPTION OF THE DRAWINGS

FIG. 2 is a summary of intermediate and definitive hosts for different apicomplexan parasites (Wasmuth, Daub et al. 2009).

FIG. 4 represents the sequence (SEQ ID NO: 1) of an advantageous embodiment of a generated novel antimalarial fusion protein.

FIG. 8 shows A) the amino acid sequence of human wild type granzyme B (SEQ ID NO: 2) and B) the nucleic acid sequence of wild type human granzyme B (SEQ ID NO: 3).

FIG. 9 shows nucleic acid sequences of serpin B9 resistant granzyme B variants, where (A) depicts variant Gb R28K (SEQ ID NO. 4) and (B) shows the variant Gb R201A (SEQ ID NO: 5).

FIG. 10 shows the nucleic acid sequence of a further serpin B9 resistant granzyme B variant, where (A) shows the variant Gb R201K (SEQ ID NO: 6).

FIG. 11 shows the amino acid sequences of further serpin B9 resistant granzyme B variants, where (A) shows the variant with the substitution R28A (Gb R28A) (SEQ ID NO. 7); (B) shows the variant with the substitution R28K (Gb R28K) (SEQ ID NO. 8); (C) shows the variant with the substitution R201A (Gb R201A) (SEQ ID NO. 9); and (D) shows the variant with the substitution R201K (Gb R201K) (SEQ ID NO. 10).

DETAILED DESCRIPTION OF THE INVENTION

Figure 1:
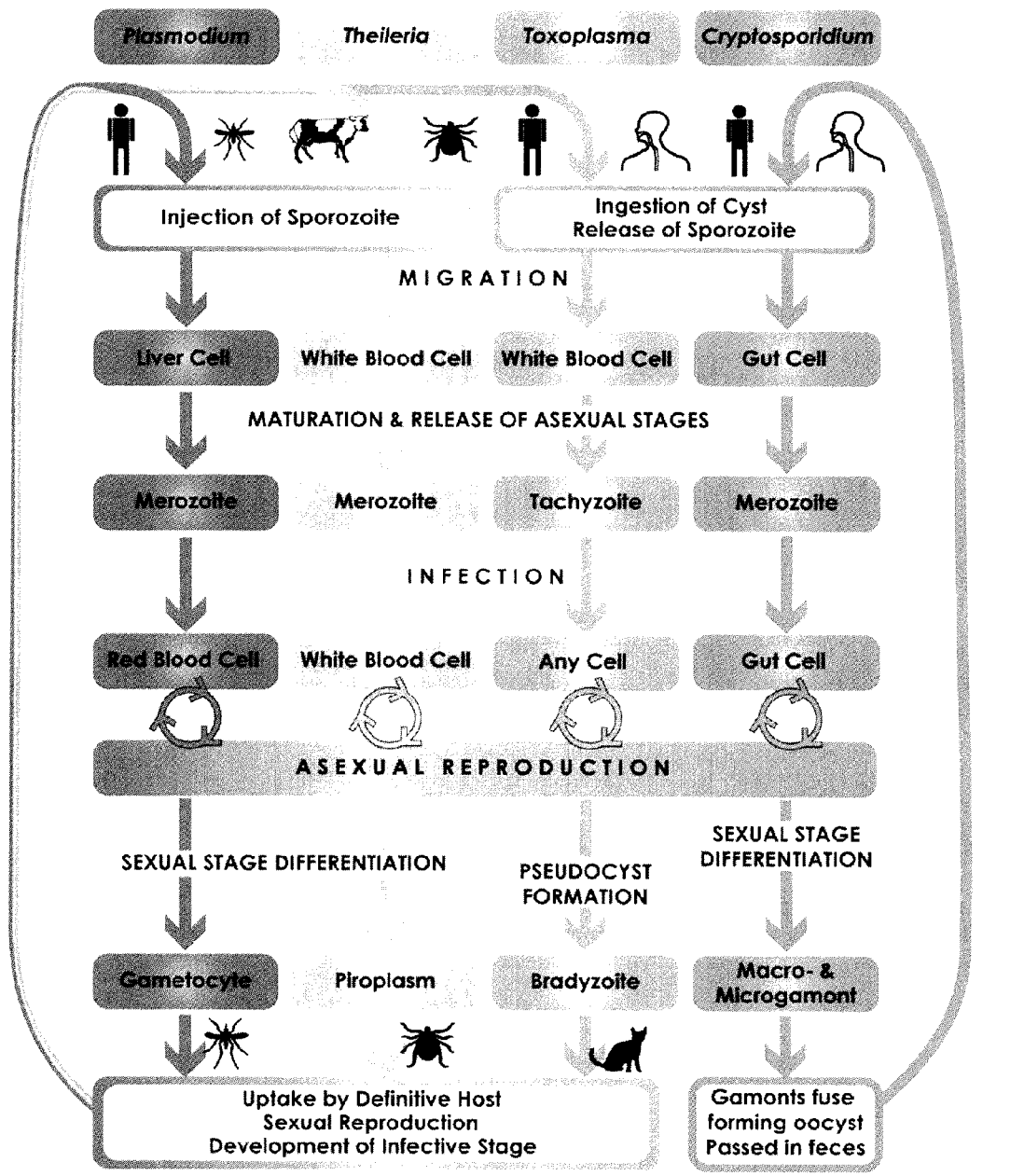
FIG. 1 is a scheme of the general life cycle of different apicomplexan parasites (Wasmuth, Daub et al. 2009).

The present application discloses therapeutically useful isolated complexes, in particular of recombinant fusion proteins suitable as human and/or animal drugs against a parasite of the phylum Apicomplexa, in particular against *P. falciparum* comprising at least one component A and at least one component B, characterized in that component A has a binding activity for cellular surface structures presented on the surface of a parasite of the phylum Apicomplexa or for parasitic antigens presented on a parasitized host cell, and component B is a compound, in particular a polypeptide having anti-parasitic activity. In particular, the present disclosure relates to the use of antibody-mediated anti-parasitic reagents based on Granzyme B (Gb) for malaria treatment.

The present disclosure pertains to isolated/purified complexes, in particular isolated recombinant fusion proteins, as anti-parasitic molecules for the therapeutic use against for example malarial infections. In some advantageous embodiments, the complexes according to the present disclosure are valuable drugs for the treatment of malaria, potentially also against multiple drug resistant strains of *P. falciparum*.

An advantageous embodiment of the present disclosure relates to isolated/purified complexes, in particular isolated recombinant fusion proteins, comprising at least one component A and at least one component B, characterized in that component A has a binding activity for cellular surface structures presented on the surface of a parasite of the phylum Apicomplexa or for parasitic antigens presented on a parasitized host cell, and component B is a compound having anti-parasitic activity.

The terms "recombinant fusion protein" and "fusion protein" are used herein interchangeably to refer for example to a protein produced by recombinant technology which comprises segments i.e. amino acid sequences, from heterologous sources, such as different proteins or different organisms. The segments are joined either directly or indirectly to each other via peptide bonds. By indirect joining it is meant that an intervening amino acid sequence, such as a peptide linker is juxtaposed between segments forming the fusion protein. A recombinant fusion protein is encoded by a nucleotide sequence, which is obtained by genetically joining nucleotide sequences derived from different regions of one gene and/or by joining nucleotide sequences derived from two or more separate genes. These nucleotide sequences can be derived from a parasite of the phylum Apicomplexa and in particular derived from *P. falciparum*, but they may also be derived from other organisms, the plasmids used for the cloning procedures or from other nucleotide sequences.

Furthermore, the encoding nucleotide sequences may be synthesized in vitro without the need for initial template DNA samples e.g. by oligonucleotide synthesis from digital genetic sequences and subsequent annealing of the resultant fragments. Desired protein sequences can be "reverse translated" e.g. using appropriate software tools. Due to the degeneracy of the universal genetic code, synonymous codons within the open-reading frame (i.e. the recombinant protein coding region) can be exchanged in different ways, e.g. to remove cis-acting instability elements (e.g. AUUUA), to remove, introduce or modify the secondary and tertiary mRNA structures (e.g. pseudoknots, stem-loops, . . . ), to avoid self-complementary regions that might trigger post-transcriptional gene silencing (PGTS), to change the overall AT:GC content, or to adjust the codon-usage to the expression host. Such changes can be designed manually or by using appropriate software tools or through a combination.

A recombinant fusion protein comprising a polypeptide having binding activity for cellular surface structures presented on the surface of a parasite of the phylum Apicomplexa, in particular to a Apicomplexa surface protein, in particular to a *Plasmodium* surface protein can be a recombinant product prepared using recombinant DNA methodology and expression in a suitable host cell, as is known in the art (see for example (Sambrook and Russell 2001).

In an advantageous embodiment, the fusion proteins are isolated fusion proteins. The term "isolated" when used in relation to a nucleic acid or protein refers to a nucleic acid sequence or protein that is identified and separated from at least one contaminant (nucleic acid or protein, respectively) with which it is ordinarily associated in its natural source. Isolated nucleic acid or protein is present in a form or setting that is different from that in which it is found in nature. In contrast, non-isolated nucleic acids or proteins are found in the state they exist in nature.

According to the present disclosure, the component A and component B are linked to each other in a complex. "Linked" refers to non-covalent or covalent bonding between two or more molecules. Linking may be direct or indirect. Two molecules are indirectly linked when the two molecules are linked via a connecting molecule (linker). Two molecules are directly linked when there is no intervening molecule linking them. As mentioned above, the isolated protein domains are linked either directly or indirectly to each other, preferably via peptide bonds or disulfide bonds. An example of indirect covalent linking is that an intervening amino acid sequence, such as a peptide linker is juxtaposed between segments forming the fusion protein.

In some embodiments, the components A and B are directly linked to each other. In other embodiments, the components are indirectly linked to each other via a linker, wherein in some examples the linker is a polypeptide with a size of less or equal twenty amino acids, in particular 2 to 6 amino acids.

The Apicomplexa (also referred to as Apicomplexia) are a large group of protists, most of which possess a unique organelle called apicoplast and an apical complex structure involved in penetrating a host's cell. They are a diverse group including organisms such as coccidia, gregarines, piroplasms, haemogregarines, and plasmodia (*P. falciparum, Plasmodium vivax, Plasmodium ovale, Plasmodium malariae, Plasmodium knowlesi*). Diseases caused by apicomplexan organisms include, but are not limited to Babesiosis (*Babesia*), Malaria (*Plasmodium*), Coccidian diseases including Cryptosporidiosis (*Cryptosporidium parvum*), Cyclosporiasis (*Cyclospora cayetanensis*), Isosporiasis (*Isospora belli*) and Toxoplasmosis (*Toxoplasma gondii*).

In advantageous embodiments, the complex, in particular the recombinant fusion proteins as well as the compositions according to the present disclosure are suitable as human and/or animal drugs against a parasite of the genus *Plasmodium* including *P. falciparum, Plasmodium vivax, Plasmodium malariae* and/or *Plasmodium ovale*. In an advantageous embodiment, the parasite is *P. falciparum*.

Cellular surface structures presented on the surface of the parasite of the phylum Apicomplexa like Apicomplexa surface proteins are preferably membrane-bound or associated proteins or proteins known to be secreted. These proteins can e.g. be identified by analyzing the Genome or known genes for the presence of an N-terminal signal peptide, the presence of a PEXEL motif, the presence of a GPI anchor motif, or the presence of one or more transmembrane domains using generally available software tools. These proteins and their homologues e.g. include but are not limited to:

CelTOS (cell traversal protein for ookinetes and sporozoites), Antigen 2 (PfAg2, PvAg2, PoAg2, etc.)
  CSP (circumsporozoite protein)
  EBA175 (Erythrocyte binding antigen 175)
  EXP1 (Exported Protein 1); synonyms: CRA1 (Circumsporozoite-Related Antigen-1/Cross-Reactive Antigen-1), AG 5.1 (Exported antigen 5.1), QF119
  MSP1 (Merozoite surface protein 1); synonyms: MSA1 (Merozoite surface antigen 1), PMMSA, p190, p195, gp190, gp195
  MSP2 (Merozoite surface protein 2);
  MSP3 (Merozoite surface protein 3); synonym: SPAM (secreted polymorphic antigen associated with the merozoite)
  MSP4 (Merozoite surface protein 4)
  MSP5 (Merozoite surface protein 5)
  MSP7 (Merozoite surface protein 7)
  MSP8 (Merozoite surface protein 8)
  MSP9 (Merozoite surface protein 9)
  MSP10 (Merozoite surface protein 10)
  MTRAP (merozoite TRAP homologue, merozoite TRAP homolog, merozoite TRAP-like protein)
  Pf38; synonym: 6-cysteine protein
  Rh2a (Reticulocyte binding protein 2 homolog a)
  Rh2b (Reticulocyte binding protein 2 homologue b)
  Rh4 (Reticulocyte binding protein homologue 4)
  Rh5 (Reticulocyte binding protein homologue 5)
  Ripr, PfRipr (Rh5 interacting protein)
  Ron2 (rhoptry neck protein 2)
  Ron4 (rhoptry neck protein 4)
  Ron5 (rhoptry neck protein 5)
  Ron6 (rhoptry neck protein 6)
  TRAMP (thrombospondin-related apical membrane protein); synonym: PTRAMP
  TRAP (Thrombospondin-related anonymous protein); synonym: SSP2 (Sporozoite Surface Protein 2)
  AMA1 (apical membrane antigen 1)
  GLURP (Glutamine-rich protein)
  RhopH2 (High Molecular Weight Rhoptry Protein-2)
  RhopH3 (High Molecular Weight Rhoptry Protein-3)

In some advantageous embodiments, the complex, in particular the fusion proteins or the compositions according to the present disclosure are directed to cellular surface structures, wherein the the cellular surface structures are presented on the surface of the parasite in at least one main stage of the Apicomplexa life cycle stages like the pre-erythrocytic stage and/or the blood stage. Preferably, the *P. falciparum* surface protein is presented on the surface of the parasite in the pre-erythrocytic stage and/or the blood stage.

The Pre-Erythrocytic Main Stage:
a) Sporozoite

The sporozoite remains in the bloodstream for a very short period of time before invading a hepatocyte. Examples for *Plasmodium* protein antigens expressed in the sporozoite are the circumsporozoite protein (CSP), the major constituent of the outer membrane of the sporozoite (Nussenzweig and Nussenzweig., 1989). Induced antibodies may be able to block the binding and the entrance of the sporozoite into the hepatocyte.

b) Liver Stage

During this stage, immunity is mostly mediated by cellular-dependent mechanisms involving CD8+ T cells, CD4+ T cells, natural killer (NK) cells and yδ T cells. CSP is expressed both in the sporozoite and during the liver stage. So, much of the research involving CSP has switched from the immunodominant repeats inducing humoral response to regions that are able to induce cytotoxic T-cell responses. Other identified liver-stage antigens include liver-stage antigen-1 (LSA-1), LSA-2, LSA-3, SALSA and STARP, among others (Garcia, Puentes et al. 2006)

The Asexual Blood Main Stage:
c) Merozoite

Besides the sporozoite, the merozoite is the only stage in the human host in which the malaria parasite is extracellular. In contrast to the sporozoite, several cycles of merozoite release will occur during a malaria infection, making them often available. A major ligand in *P. falciparum* is the erythrocyte-binding antigen-175 (EBA-175), located in the microneme (Sim, Toyoshima et al. 1992). Several merozoite surface proteins (MSPs) have been identified, but for most of them their function still has to be further elucidated. In the case of the major MSP, named MSP-1, a role has been postulated in merozoite binding to the RBC and in the subsequent biochemical mechanisms involved in invasion. This protein is synthesized as a precursor of 185-210 kDa in the late schizont stage and is processed to generate several polypeptides of varied molecular weights. A 42 kDa polypeptide (MSP1-42) is kept attached to the merozoite membrane, and it is further processed to generate a 19 kDa polypeptide (MSP1-19), which goes into the host cell. Besides MSP-1, at least eight other MSPs have been described in *P. falciparum*: MSP-2, MSP-3, MSP-4, MSP-5, MSP-6, MSP-7, MSP-8 and MSP-10. Another merozoite surface-associated antigen is the acidic-basic repeat antigen (ABRA). Proteins located in merozoite apical organelles have also been identified (e.g. the rhoptry proteins apical membrane antigen-1 (AMA-1), rhoptry-associated protein-1 (RAP-1) and RAP-2).

d) Infected RBC

Once it has invaded the RBC, the parasite is supposed to have found a safer place to stay. One of the most studied molecules is the ring erythrocyte surface antigen (RESA). Further, the serine-rich protein (SERP or SERA) is a soluble protein expressed in the schizont stage and secreted in the parasitophorous vacuole. Other proteins that are located on the RBC membrane are the erythrocyte membrane protein-1 (EMP-1), EMP-2 and EMP-3. PfEMP-1, which binds to the receptors such as CD36 in the endothelium, is a family of proteins encoded by the so-called var genes.

In some embodiments, component A has a binding activity either for cellular surface structures presented on the surface of a parasite of the phylum Apicomplexa or for parasitic antigens presented on a parasitized host cell.

As used herein a "parasitized host cell" is defined as a human or animal cell infected by an Apicomplex parasite, in particular infected with P. falciparum. In the case of the malaria parasite, the infected host cells differ according to the main stage of the parasite. In the pre-erythrocytic stage, parasites infect the human liver cells. Sporozoites are injected into the blood and lymph of the host. Via the blood stream, they are carried to the liver and infect the hepatocytes. In the erythrocytic stage of the malaria life cycle, the parasites infect erythrocytes and reticulocytes in the blood system, thus these infected erythrocytes and reticulocytes represent the parasitized host cells at this stage.

Parasite antigens are defined as antigens encoded by the parasite genome (Gardner, Hall N et al. 2002).

In the pre-erythrocytic stage of the malaria life cycle:

In the erythrocytic stage of the malaria life cycle, parasite antigens presented on the surface of the parasitized host cells include, but are not limited to, the secretome of the malaria parasite (Marti, Good et al. 2004, Hiller, Bhattacharjee et al. 2004). The antigens presented on the malaria surface of the parasitized erythrocytes have been described before (Smith and Craig., 2005). These antigens comprise, but are not limited to, the protein families PfEMP1, rifs, stevors, kahrps, clag9, rsp1 and rsp2.

During the pre-erythrocytic life stage, parasite antigens comprise the transcriptome (~2000 genes), proteome (~800 proteins) and the secretome (~80 proteins containing a signal peptide) of the malaria parasite (Tarun, Peng et al. 2008).

The present disclosure is also directed to compositions suitable as drugs against a parasite of the phylum Apicomplexa comprising a plurality, in particular at least two complexes, in particular at least two isolated recombinant fusion proteins directed to at least two different Apicomplexa surface proteins presented on the surface of the parasite, in the same or in at least two different main stages of the parasite life cycle.

As mentioned above, component A of the fusion proteins according to the present disclosure have a binding activity for cellular surface structures presented on the surface of a parasite of the phylum Apicomplexa.

The terms "component having a binding activity for cellular surface structures presented on the surface" or "target cell-specific binding component" are used herein interchangeably and refer to polypeptides having a binding activity for cellular surface structures. For example, the polypeptide based ligands may be provided with a cell targeting moiety that is a moiety that binds to and/or is internalized and/or is co-imported by only a selected population of cells such as cells of a parasite of the phylum Apicomplexa, in particular of a parasite of the genus Plasmodium including P. falciparum, Plasmodium vivax, Plasmodium malariae, P. knowlesi and/or Plasmodium ovale. In an advantageous embodiment, the parasite is P. falciparum.

Such a cell targeting may, for example, comprise an antibody, a growth factor, a hormone, a cytokine, an aptamer, an avimer, or derivates thereof that binds to a cell surface protein. Examples for binding moieties comprised in the ligand are affinity moieties from affinity substances or affinity substances in their entirety selected from the group consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof. In particular the target cell-specific binding component specifically binds to an antigen i.e. a cellular surface structure of P. falciparum presented in one or more main Plasmodium life cycle stages.

In an advantageous embodiment, the target cell-specific binding component is an antibody or an antibody fragment selected from the group consisting of a monoclonal antibody, Fab, scFv; single domain, or a fragment thereof, bis scFv, Fab2, Fab3, minibody, diabody, triplebody, tetrabody and tandab.

An antibody is in particular specific for a particular antigen if it binds that particular antigen in preference to other antigens. In particular, the antibody may not show any significant binding to molecules other than that particular antigen, and specificity may be defined by the difference in affinity between the target antigen and other non-target antigens. An antibody may also be specific for a particular epitope which may be carried by a number of antigens, in which case the antibody will be able to bind to the various antigens carrying that epitope. For example, specific binding may exist when the dissociation constant for a dimeric complex of antibody and antigen is 1 µM, preferably 100 nM and most preferably 1 nM or lower.

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain (VL) and variable heavy chain (VH) refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to $V_H$-$C_{H}1$ by a disulfide bond. The F(ab)'2 may be reduced under mild conditions to break the disulfide linkage in the hinge region thereby converting the (Fab')2 dimer into two Fab' monomers. The Fab' monomer is essentially a Fab with part of the hinge region (Paul 1993) While various antibody fragments are defined in terms of the digestion of an intact antibody, one of skill will appreciate that such Fab' fragments may be synthesized de novo either chemically or by utilizing recombinant DNA technology. Thus, the term antibody, as used herein also includes antibody fragments either produced by the modification of whole antibodies or synthesized de novo using recombinant DNA technologies. Preferred antibodies include single chain antibodies (antibodies that exist as a single polypeptide chain), more preferably single chain Fv antibodies (scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker (Huston, Levinson et al. 1988). While the VH and VL are connected to each as a single polypeptide chain, the VH and VL domains associate non-covalently.

An "antigen-binding site" or "binding moiety" in an antibody or antibody fragment refers to the part of an immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences which are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by (Kabat 1987)

The phrase "specifically binds to an antigen" or "specifically binds to a cellular surface structure" refers to a binding reaction, which is determinative of the presence of an antigen protein in the presence of a heterogeneous population of proteins and other biologics. Thus, under designated immunoassay conditions, the specified antibodies or antibody fragments comprised in the fusion protein according to the present disclosure bind to the specific antigen and do not bind in a significant amount to other proteins present in the sample.

In an advantageous embodiment, the target cell-specific binding component is an antibody fragment, in particular a single-chain variable fragment (scFv).

As used herein, the term "single chain variable fragment" (scFv) refers to antibodies prepared by determining the binding domains (both heavy and light chains) of a binding antibody, and supplying a linking moiety, which permits preservation of the binding function. This forms, in essence, a radically abbreviated antibody, having only that part of the variable domain necessary for binding to the antigen. Determination and construction of single chain antibodies are described in U.S. Pat. No. 4,946,778 by Ladner et al.

In an advantageous embodiment, the scFv specifically binds to the merozoite surface protein 4 (MSP4). In a further embodiment, the scFv is directed in VL-VH or VH-VL orientation.

The terms "polypeptide", "peptide", or "protein" are used interchangeably herein to designate a linear series of amino acid residues connected one to the other by peptide bonds between the alpha-amino and carboxyl groups of adjacent residues. The amino acid residues are preferably in the natural "L" isomeric form. However, residues in the "D" isomeric form can be substituted for any L-amino acid residue, as long as the desired functional property is retained by the polypeptide. In addition, the amino acids, in addition to the 20 "standard" amino acids, include modified and unusual amino acids.

The complex according to the present disclosure comprise at least one component A and at least one component B, characterized in that component B may be a polypeptide having anti-parasitic activity.

Then term "anti-parasitic activity" means destroying or inhibiting the growth and/or reproduction of parasites of the phylum Apicomplexa, in particular of a parasite of the genus Plasmodium including *P. falciparum, Plasmodium vivax, Plasmodium malariae, P. knowlesi* and/or *Plasmodium ovale*. In an advantageous embodiment, the parasite is *P. falciparum* in at least one main life cycle stage. In particular, the polypeptide having anti-parasitic activity is able to destroy or inhibit the growth and/or reproduction of *P. falciparum*.

A compound or a substance can be tested for its anti-parasitic activity in a 72-h assay described in Kreidenweiss, A., P. G. Kremsner and B. Mordmuller (2008). "Comprehensive study of proteasome inhibitors against *Plasmodium falciparum* laboratory strains and field isolates from Gabon." Malar J 7: 187.

According to the above-mentioned assay, the complexes and compositions of the present disclosure comprise an anti-parasitic activity.

In some advantageous embodiments, the compound having anti-parasitic activity is a polypeptide selected from the group consisting of a protease, a serine protease, a bacteria-originated toxic compound such as the *Pseudomonas aeruginosa* exotoxin A, a human hydrolase such as angiogenin, a cytoskeleton-associated protein such as the microtubule-associated protein tau, a photosensitizer or a plant-originated toxin such as Ricin A, or variants or functional fragments thereof.

In further embodiments, the drugs considered as component B include all kinds of substances that can display their mode of action on the parasite and that are likely to be more effective when transported to a particular site of the parasite. Preferentially these are compounds with proven efficacy e.g. as chemotherapeutical agents. They may be selected from the group of alkylating agents (e.g. cyclophosphamide, cholrambucil), anthracyclins (doxorubicin, daunomycin), maytansinoids (maytansinoid DM1), anti-metabolites, plant alkaloids and terpenoids as the *Vinca* alkaloids (vinblastine, vincristine vinorebline, vindesin) Podophyllotoxin and derivatives hereof and taxanes (paclitaxel, docetaxel, taxotere) or topoisomerase inhibitors (camptothecins), synthetic toxins as ellipticine analogs or snythetic analogs of tumor antibiotics as duocarmycin or CC1065, other tubulin binding agents as halichondrin B, hemiasterlins and dolastatins or analogs as monomethyl-auristatin E; component B may also be selected from the group of small molecules having cytotoxic/cytostatic activities like alkylating agents (like Cyclophosphamide, Mechlorethamine, Chlorambucil, Melphalan) or anthracyclines (like Danorubicin, Doxorubicin, Epirubicin, Idarubicin, Mitoxantrone, Valrubicin) or cytoskeletal disruptors (like Paclitaxel, Docetaxel) or Epothilones (like) or Inhibitors of topoisomerase II (like Etoposide, Teniposide, Tafluposide) or nucleotide analogs and precursor analogs (like azacididine, azathioprine, capecitabine, cytarabine, doxofluridine, fluorouracil, gemcitabine, mercaptopurine, methotrexate, tioguanine) or peptide antibiotics (like bleomycin) or platinum-based agents (like carboplatin, cisplatin, oxaliplatin) or retinoids (like all-trans retinoic acid) or vinca alkaloids and derivatives (like vinblastine, vincristine, vindestine, vinorelbine), beta ray emitting nuclides like Iodine-131, Yttrium-90, Lutetium-177, from the group of Aromatase Inhibitors (like Aminoglutethimide, Anastrozole, Letrozole, Vorozole, Exemestane, 4-androstene-3,6,17-trione, 1,4,6-androstatrien-3,17-dione, Formestane, Testolactone), Carbonic Anhydrase Inhibitors (like Acetazolamide, Methazolamide, Dorzolamide, Topiramate), Cholinesterase Inhibitors (Organophosphates like Metrifonate, Carbamates like Physostigmine, Neostigmine, Pyridostigmine, Ambenonium, Demarcarium, Rivastigmine, Phananthrine like Galantamine, Piperidine like Donepezil, Tacrine, Edophonium, or Phenothiazines), Cyclooxygenase Inhibitors (like Celecoxib, Rofecoxib, Etoricoxib, Acetaminophen, Diclofenac, Ibuprofen), Folic Acid Antagonists (like Methotrexate), Hydroxymethylglutaryl-CoA Reductase Inhibitors (like Atorvastatin, Cerivastatin, Fluvastatin, Lovastatin, Mevastatin, Pitavastatin, Pravastatin, Rosuvastatin, Simvastatin, Vytorin, Advicor, Caduet), Integrase Inhibitors (like Raltegravir, Elvitegravir), Lipoxygenase Inhibitors (like Zileutron), Monoamine Oxidase Inhibitors (like Isocarboxazid, Moclobemide, Phenelzine, Tranylcypromine, Selegiline, Rasagiline, Nialamide, Iproniazid, Iproclozide, Toloxatone, Linezolid, Tryptamines, Dienolide, Detxtroamphetamine), Nucleic Acid Synthesis Inhibitors, Phosphodiesterase Inhibitors (like Caffeine, Theopyline, 3-isobutyl-1-methylxanthine, Vinpocetine, EHNA, Enoximone, Lirinone, PDE3, Mesembrine, Rolipram, Ibudilast, Sildenafil, Tadalafil, Vardenafil, Udenafil, Avanafil), Protease Inhibitors (like Saquinavir, Ritonavir, Idinavir, Nelfinavir, Amprenavir, Lopinavir, Atazanavir, Fosamprenavir, Tipranavir, Darunavir), Protein Kinase Inhibitors (like Imatinib, Geftinib, Pegaptanib, Sorafenib, Dasatinib, Sunitinib, Erlotinib, Nilotinib, Lapatinib), Protein Synthesis Inhibitors (like Anisomycin, Cycloheximide, Chloramphenicol, Tetracycline, Streptomycin, Erythromycin, Puromycin, etc.), Proton Pump Inhibitors (like Omeprazole, Lansoprazole, Esomeprazole, Pantoprazole, Rabeprazole), from the group of oligonucleotides nucleic acids like small interfering RNAs (siRNAs) or a short hairpin RNA (shRNA), an antisense DNA or RNA, a double stranded RNA (dsRNA) or a micro RNA (miRNA) might be used to down-regulate specific key elements of regulative pathways within a cell.

In a specific embodiment component B is a polymer or dendrimer carrying several cytostatic/cytotoxic agents as exemplified above like e.g. paclitaxel (or alternative methothrexat) molecules and is modified to improve biocompatibility e.g. by pegylation.

In another example the drug can be a nucleic acid or a nucleic acid analog which can exert biological activity in the targeted parasite. More specifically the nucleic acid molecule can be designed to allow the expression of an encoded protein in the targeted parasite (in the sense of a gene therapy) or to mediate RNA interference (RNAi) (an siRNA, shRNA or precursors thereof).

The component B can further be a prodrug that is activated e.g. by cellular proteases upon entry of the target cell.

The drug may further be a peptide or polypeptide that has toxic activity in the targeted cell. Examples are the ADP ribosylating enzymes *pseudomonas* exotoxin A, diphtheria-, cholera-, pertussis- and botulinotoxin. The ribosome inactivating proteins diathin, saporin, bryodin, gelonin, ricin, abrin or restrictocin. ribonucleases (Phosphodiesterases) RNAse H, angiogenin, eosinophil-derived neurotoxin (EDN), eosinophilic cationic protein, onconase and bullfrog lektin. Additional proteins that can be represented by B include prodrug activating enzymes as caliceamicin, glucoseoxidase, carboxypeptidase, alkaline phosphatase, cytosindeaminase, beta-glycosidase, beta-glucoronidase, beta-lactamase, nitroreductase, thymidinkinase or purinnucleosid phosphorylase. Further cathepsines, granzymes and combinations and possible variations of the afore mentioned protein families.

Preferred are validated toxins as ricin A, alpha sarcin (family of lectins), diphteriatoxin and *pseudomonas* exotoxin A. They have been subject of several clinical studies and their efficacy is well documented.

Component B may also represent toxic peptides as defensines, anti-fungal peptides or e.g. several peptides isolated from lumpfish or sponges.

In some embodiments, the polypeptide having anti-parasitic activity is a granzyme, in particular granzyme B, granzyme A, granzyme H, granzyme K, granzyme M, trypsin or chymotrypsin, or variants or functional fragments thereof. In an advantageous embodiment, the polypeptide having anti-parasitic activity is Granzyme B (Gb) or a variant thereof.

The term "variant" means that the enzyme has been modified from its original form (parent/wildtype, wt) but retains the same enzymatic functional characteristics.

The term "functional fragment" means a fragment or portion of the wildtype polypeptide having anti-parasitic activity that retains about the same enzymatic function or effect.

In particular, the fusion protein according to the present disclosure comprises as component B a serine protease like human Gb, a serine-dependent and aspartate-specific protease, or variants thereof.

Granzyme B (Gb) is a serine protease most commonly found in the granules of cytotoxic lymphocytes (CTLs), natural killer cells (NK cells) and cytotoxic T cells. Gb is secreted by these cells along with the pore forming protein perforin to mediate apoptosis in target cells. Granzyme B's structure consists of two 6-stranded β sheets with 3 trans domain segments. In the granules of cytotoxic lymphocytes the enzyme can exist in two glycosylated forms. The high mannose form weighs 32 kDa and the complex form, 35 kDa (Rousalova and Krepela 2010).

The term "Gb variants" means any Gb molecule obtained by site-directed or random mutagenesis, insertion, deletion, recombination and/or any other protein engineering method, which leads to Gb that differ in their amino acid sequence from the human wildtype Gb. The terms "wildtype Gb", "wildtype enzyme", or "wildtype" in accordance with the disclosure describe a serine protease enzyme with an amino acid sequence found in nature or a fragment thereof.

In particular, Gb variants comprised in fusion protein according to the present disclosure may show reduced sensitivity to an activity-inhibiting substance.

In some embodiments, the activity-inhibiting substance inhibits Gb activity, inhibits granzyme transcription, inhibits granzyme translation, increases granzyme degradation, or destabilizes granzyme. In other embodiments, the granzyme inhibitor inhibits granzyme function. The granzyme inhibitor can be a polypeptide, an anti-granzyme antibody, or a small molecule. In some specific embodiments, the polypeptide is a serpin. Serpins are endogenous serine protease inhibitors and some examples of serpin useful in the context of the present invention are SPIE, PI9, PI-6, monocyte neutrophil elastase inhibitor (MNIN), PI-8, and plasminogen activator inhibitor 2 (PAI-2). In an advantageous embodiment, the activity-inhibiting substance is serpin B9 (proteinase inhibitor 9 (PI-9)). Furthermore, in some embodiments, the activity-inhibiting substance is a virally encoded serpin, cytokine response modifier A (CrmA) of poxviruses and/or a 100 kDa assembly protein (Ad5-100K) of a human adenovirus, known as adenovirus type 5.

In particular, Gb variants comprised in fusion protein according to the present disclosure may show reduced sensitivity to activity-inhibiting substances like Serpin B9. These characteristic make them specifically useful as a part of a powerful anti-parasitic fusion protein, in particular as a part of a fusion protein according to the present disclosure. Examples of variants of the human granzyme B having serpin B9 resistants are shown in SEQ ID NO. 4, 5 and 6 (nucleic acid sequences) and SEQ ID NO. 7, 8, 9 and 10 (amino acid sequences).

In an advantageous embodiment, Gb is comprised in fusion proteins according to the present disclosure. The inventors surprisingly found that Gb bears anti-parasitic activity. The present disclosure shows the direct activity against *P. falciparum* (IC$_{50}$: 1590 nM (CI: 1197-2112 nM)).

As mentioned above, in some advantageous embodiments complexes, in particular the recombinant fusion proteins according to the present disclosure are new antimalarial fusion proteins consisting of Gb and a MSP4-specific scFv which directly targets Gb into infected erythrocytes with a 5-8-fold decreased IC$_{50}$ (176 nM (CI: 154-202 nM)).

In particular, recombinant isolated fusion proteins according to the present disclosure comprise an amino acid sequence of SEQ ID NO: 1 (FIG. 4).

In some embodiments, the fusion proteins according to present disclosure comprise the amino acid sequence of SEQ ID NO: 1, or homologous polypeptides thereof, which are produced by recombinant or synthetic methods by substitution, insertion, addition or deletion of one or more amino acid residues, or fragments thereof.

In further embodiments, the present disclosure pertains to recombinant isolated fusion proteins that are at least 85%, at least 90%, at least 95%, at least 97%, at least 98% or at least 99% identical to the amino acid sequence of SEQ ID NO: 1.

In some embodiments, the complexes, in particular the recombinant isolated fusion proteins have one or more supplementary components S in addition to the binding structure (component A) and the polypeptide having anti-parasitic activity (component B).

The component S may be selected from the group consisting of an inducible promoter capable of regulating synthetic performance, a leader sequence capable of controlling protein biosynthesis, His tag, affinity tag, translocation domain amphipathic sequence capable of translocating an apoptotic agent into a target cell, and a synthetic pro-Gb amphipathic sequence capable of intracellular activation of a granzyme.

In advantageous embodiments, the component S is a leader sequence for secretory expression and/or the component S is a enterokinase cleavage site enabling activation of a polypeptide according to the present disclosure and/or the component S is a HIS tag or affinity tag, enabling purification of the complex.

Furthermore, the present disclosure relates to nucleic acid molecules or nucleic acids encoding the complexes or parts thereof, in particular said recombinant fusion proteins according to the present disclosure as well as to vectors comprising the nucleic acid molecule and host cells comprising a nucleic acid molecule encoding said recombinant fusion protein or a vector comprising said vector. The disclosure pertains also to methods of manufacturing said fusion proteins in a recombinant expression system.

To express a fusion protein according to the present disclosure in a recombinant expression system, a DNA encoding the fusion protein or parts thereof, may be inserted into an expression vector such that the gene is operably linked to transcriptional and translational control sequences. In this context, the term "operably linked" means that a protein gene is ligated into a vector such that transcriptional and translational control sequences within the vector serve their intended function of regulating the transcription and translation of the protein gene. The expression vector and expression control sequences are chosen to be compatible with the expression host cell used. The isolated protein domain sequences are typically inserted into the same expression vector. The protein genes are inserted into the expression vector by standard methods. Additionally, the recombinant expression vector can encode a signal peptide that facilitates co-translational translocation of the nascent polypeptide chain into the endoplasmic reticulum (ER). The folded polypeptide (recombinant fusion protein according to this disclosure) may be secreted from a host cell or may be retained within the host cell. Intracellular retention or targeting can be achieved by the use of an appropriate targeting peptide such as C-terminal KDEL-tag for ER retrieval.

In general, those skilled in the art are well able to construct vectors and design protocols for recombinant gene expression (Sambrook, Maniatis et al. 1989, or later editions of this work, Ausubel 1992).

The term "vector" includes a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g. bacterial vectors having a bacterial origin of replication and episomal mammalian vectors). Other vectors (e.g. non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression system" or "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g. replication-defective retroviruses, adenoviruses and adeno-associated viruses), which serve equivalent functions.

The present disclosure is also directed to a host cell with a vector comprising the recombinant fusion proteins according to the present disclosure. The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Host cells include progeny of a single host cell, and the progeny may not necessarily be completely identical (in morphology or in total DNA complement) to the original parent cell due to natural, accidental, or deliberate mutation and/or change. A host cell includes a cell transfected or infected in vivo or in vitro with a recombinant vector or a polynucleotide of the present disclosure. A host cell, which comprises a recombinant vector of the disclosure, may also be referred to as a "recombinant host cell".

The term "host cell(s)" refers to cell(s), which may be used in a process for purifying a recombinant protein in accordance with the present disclosure. Such host cells carry the protein of interest (POI). A host cell may also be referred to as a protein-expressing cell. A host cell, according to the present invention, may be, but is not limited to, prokaryotic cells, eukaryotic cells, archaebacteria, bacterial cells, insect cells, yeast, mammal cells, and/or plant cells. Bacteria envisioned as host cells can be either gram-negative or gram-positive, e.g. *Escherichia coli, Erwinia* sp., *Klebsiella* sp., *Lactobacillus* sp., *Bacillus subtilis* or *Pseudomonas fluorescens*. Typical yeast host cells are selected from the group consisting of *Saccharomyces cerevisiae, Hansenula polymorpha* and *Pichia pastoris*. In some advantageous embodiments, the host cell is a HEK293 cell, such as a HEK293T cell or a HEK293-6E cell.

The recombinant isolated fusion proteins of the present disclosure can be used with a "pharmaceutically acceptable carrier" which includes any and all solvents, dispersion media, coatings, surfactants, antioxidants, preservatives (e.g. antibacterial agents, antifungal agents, antiprotozoan agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art.

A pharmaceutically acceptable carrier is preferably formulated for administration to a human, although in certain embodiments it may be desirable to use a pharmaceutically acceptable carrier that is formulated for administration to a non-human animal, such as a canine, but which would not be acceptable (e.g. due to governmental regulations) for administration to a human. Except insofar as any conventional carrier is incompatible with the active ingredient, its use in the therapeutic or pharmaceutical compositions is contemplated.

The actual dosage amount of a composition of the present disclosure administered to a subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

Apicomplexa are responsible for a number of important human diseases including malaria, toxoplasmosis, cryptosporidiosis and cyclosporidiosis. Therefore, in the recombinant fusion proteins according to the disclosure are used for treating malaria, toxoplasmosis, cryptosporidiosis and cyclosporidiosis, in particular for treating malaria.

Figure 3:
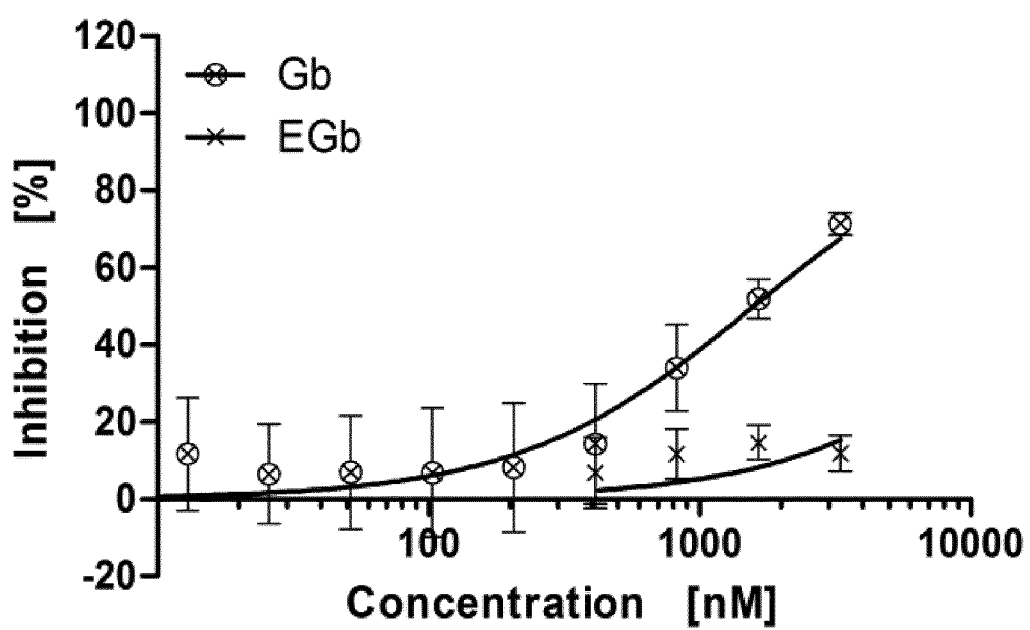
FIG. 3 is a diagram showing the results from a 72-h drug susceptibility assay on *P. falciparum* 3D7A.

FIG. 3 shows the susceptibility of Pf 3D7A towards active Gb (⊕) in a 72-h drug susceptibility assay starting at ring-stage. Inactive EGb (x) does not inhibit the growth of the parasites. The data represent the mean±SD of two technical replicates measured in duplicate, respectively.

FIG. 4 shows the sequence of the EGb-2.44scFv fusion protein and illustrates the different domains, motifs and tags (SEQ ID NO. 1).

Figure 5:
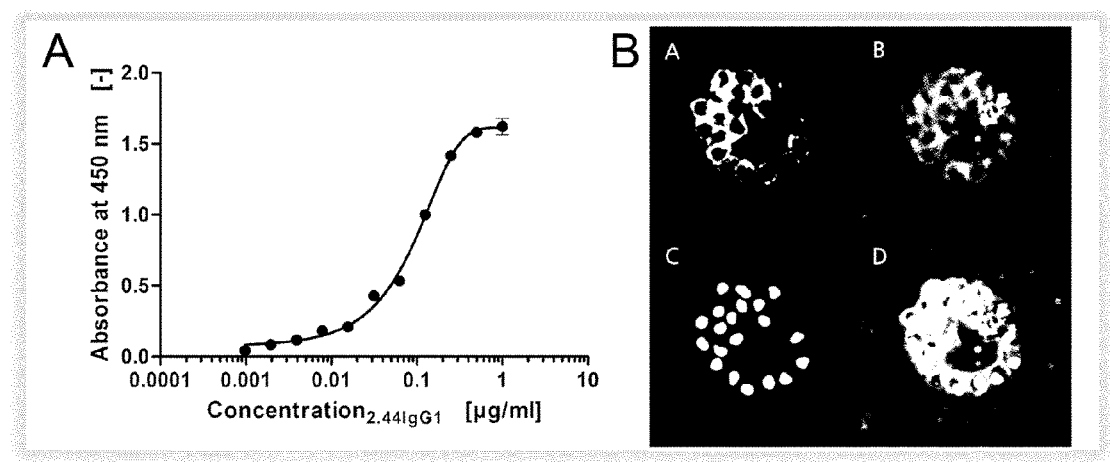
FIG. 5 demonstrates the specific binding of the antibody 2.44IgG1 to PfMSP4, where (A) shows results of ELISA binding assays of the recombinant chimeric antibody 2.44IgG1 to MSP4 and (B) shows results of immunofluorescence assays depicting the binding of 2.44IgG1 to MSP4.

FIG. 5 shows the specific binding of the recombinant chimeric antibody 2.44IgG1 to MSP4 and to the merozoite surface.

In (A), an ELISA was performed on EIA plates coated with recombinant MSP4. Serial dilutions of recombinant chimeric antibody 2.44IgG1 were added and subsequently detected using a goat anti-human IgG antibody (Jackson Immuno-Research, Fc-specific and conjugated to a peroxidase). The reactions were visualized with TMB (Invitrogen) for 5 min and then the reaction was stopped with 1 M HCl. The absorbance was read at 450 nm. The data represent the mean±the range of one representative experiment in duplicate.

In (B), specific binding of 2.44IgG1 to MSP4 was verified by immunofluorescence assay using methanol-fixed *P. falciparum* 3D7A mature schizonts. (A) Parasites were co-stained with polyclonal rabbit anti-AMA1 antibody (BG98), and visualized with a goat anti-rabbitAlexaFluor®488 secondary antibody. (B) The recombinant chimeric antibody 2.44IgG1 was visualized with a goat anti-human IgGAlexaFluor®647 secondary antibody. (C) Nuclei were stained with 10 µg/ml Hoechst33342. (D) The overlay image includes the bright field image.

Figure 6:
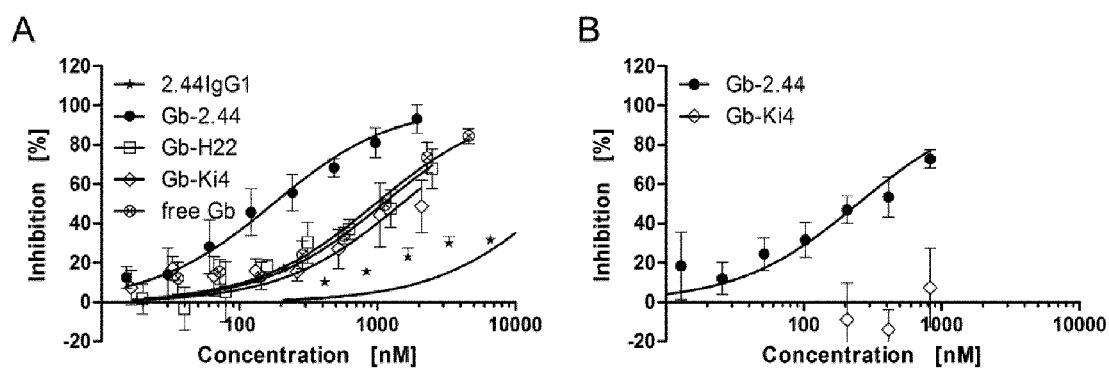
FIG. 6 is a diagram showing the results from a 48-h drug susceptibility assay on (A) *P. falciparum* 3D7A and (B) the multi-drug-resistant strain *P. falciparum* K1.

FIG. 6 shows the enhanced inhibition of parasite growth mediated by Gb fused to an MSP4-specific scFv in a 48-h drug susceptibility assay from schizont to schizont stage. Schizonts were incubated in the presence of the MSP4-specific fusion Gb-2.44 (•), two unrelated fusions named Gb-H22 ( ) and Gb-Ki4 (◇), non-fused Gb (|) and the chimeric MSP4-specific antibody 2.44IgG1 (*) for 48 h. The assay was carried out on *P. falciparum* 3D7A (A) and a the multi-drug-resistant strain, *P. falciparum* K1 (B). Data represent the mean±SD of three experiments in triplicate (*P. falciparum* 3D7A) or one experiment in triplicate (Pf K1).

Figure 7:
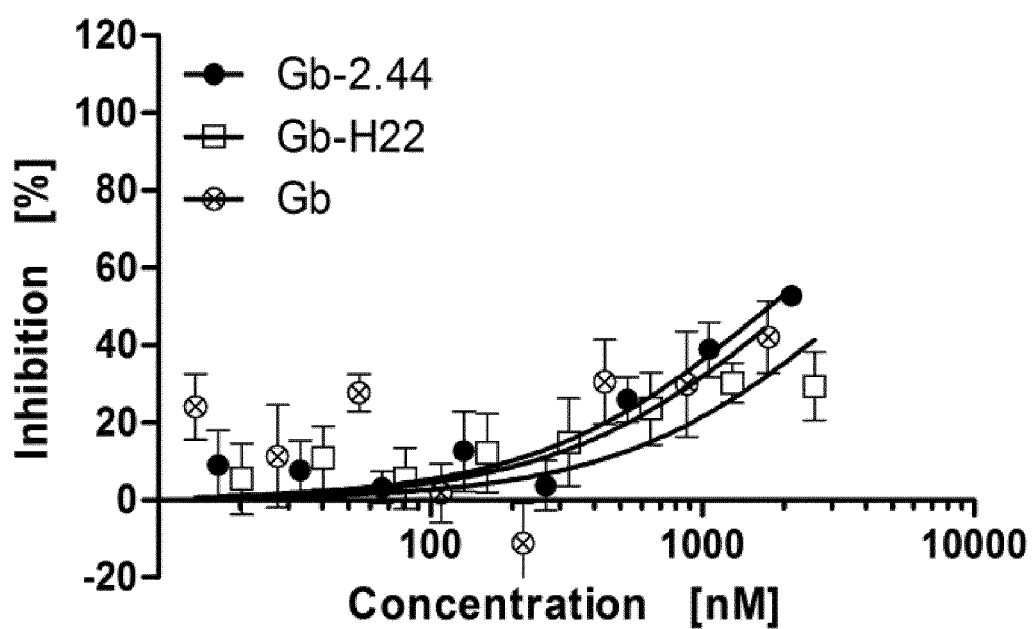
FIG. 7 is a diagram showing the results from a 30-h drug susceptibility assay on *P. falciparum* 3D7A.

FIG. 7 shows the dependence of the enhanced growth inhibition on the co-import of Gb-2.44 (•) in comparison to the unrelated fusion protein Gb-H22 (◇) or non-fused Gb (⊕). Parasites were incubated for 30 h starting at ring stage to mature schizonts, thus leaving out a rupture- or merozoite invasion-step. Data represent the mean±SD of two experiments in triplicate.

In summary, the present disclosure relates to fusion proteins comprising at least one component A and at least one component B, characterized in that component A has a binding activity for cellular surface structures presented on the surface of a parasite of the phylum Apicomplexa, and component B is a polypeptide having anti-parasitic activity, wherein the fusion proteins may be recombinant fusion proteins, and/or
  the parasite of the phylum Apicomplexa may be a parasite of the genus *Plasmodium*, and/or
  the parasite of the genus *Plasmodium* may be selected from the group consisting of *P. falciparum, P. vivax, P. ovale, P. knowlesi* and *P. malariae*, and/or
  the parasite of the genus *Plasmodium* may be *P. falciparum*, and/or the cellular surface structures may be presented on the surface of the parasite in at least one main stage of the Apicomplexa life cycle stages like the pre-erythrocytic stage or the blood stage, and/or the *P. falciparum* surface protein may be presented on the surface of the parasite in the pre-erythrocytic stage and/or the blood stage, and/or the cellular surface structure may be a surface protein, and/or the cellular surface structure may be selected from the group consisting of CelTos, CSP, EXP1, MSP1, MSP2, MSP3, MSP4, MSP5, MSP7, MSP8, MSP9, MSP10, mTRAP, Pf38, Rh1, Rh2a, Rh2b, Rh4, Rh5, Ripr, RON2, RON4, RON5, PfRON6, TRAMP, AMA1, GLURP, RhopH2 and RhopH3, and/or the component A may be selected from the group of actively binding structures consisting of antibodies, antibody fragments, receptor ligands, enzyme substrates, lectins, cytokines, lymphokines, interleukins, angiogenic or virulence factors, allergens, peptidic allergens, recombinant allergens, allergen-idiotypical antibodies, autoimmune-provoking structures, tissue-rejection-inducing structures, immunoglobulin constant regions and their derivatives, mutants or combinations thereof, and/or the component A may be a binding structure selected from the group consisting of an antibody or an antibody fragment selected from the group consisting of Fab, scFv; single domain, or a fragment thereof, bis scFv, Fab2, Fab3, minibody, diabody, triabody, tetrabody and tandab, and/or the component A may be a single-chain variable fragment (scFv), and/or the scFv may be specific for the epidermal growth-factor-like domain of the merozoite surface protein 4 (MSP4), and/or the scFv may be directed in VL-VH or VH-VL orientation, and/or the polypeptide having anti-parasitic activity may be selected from the group consisting of a protease, a serine protease a bacteria-originated toxic compound such as the *Pseudomonas aeruginosa* exotoxin A, a human hydrolase such as angiogenin, a cytoskeleton-associated protein such as the microtubule-associated protein tau, a photosensitizer and a plant-originated toxin such as Ricin A, and variants or functional fragments thereof, and/or the polypeptide having anti-parasitic activity may be a granzyme, in particular granzyme B, granzyme A, granzyme H, granzyme K, granzyme M, trypsin or chymotrypsin, and/or the polypeptide having anti-parasitic activity may be a wild type human granzyme B or a variant or a functional fragment thereof, in particular a serpin B9 resistant variant, and/or the fusion protein may comprise the amino acid sequence of SEQ ID NO: 1, or homologous polypeptides thereof, which are produced by recombinant or synthetic methods by substitution, insertion, addition or deletion of one or more amino acid residues, or fragments thereof, and/or the fusion proteins may contain one or more supplementary components S in addition to said components A and B, and/or the component S may be selected from the group consisting of an inducible promoter capable of regulating synthetic performance, a leader sequence capable of controlling protein biosynthesis, a HIS tag, an affinity tag and a translocation domain amphiphatic sequence capable of translocating a fusion protein into a target cell.

The present disclosure pertains further to nucleic acid molecules coding for a fusion protein according to the present disclosure. Furthermore, the present disclosure pertains to vectors carrying at least one of said nucleic acid molecules. Furthermore, the present disclosure pertains to cells transfected with at least one of said vectors.

The present disclosure relates further to medicaments comprising a fusion protein according to the present disclosure in combination with a pharmacologically acceptable carrier or diluent.

The present disclosure relates further to the use a fusion protein according to the present disclosure for the treatment of malaria.

Furthermore, the present disclosure relates to methods for preparing the fusion protein according to the present disclosure wherein the method comprises culturing a cell to the present disclosure and isolating the fusion protein from the cell culture.

The following methods and examples are offered for illustrative purposes only, and are not intended to limit the scope of the present disclosure in any way.

METHODS AND EXAMPLES

In the following examples, materials and methods of the present disclosure are provided including the determination of binding and inhibiting properties of the fusion proteins according to the present disclosure. It should be understood that these examples are for illustrative purpose only and are not to be construed as limiting this disclosure in any manner. All publications, patents, and patent applications cited herein are hereby incorporated by reference in their entirety for all purposes.

Example 1: Anti-Parasitic Effect of Recombinant Gb and Gb-Based Fusion Proteins on *P. Falciparum*

In the following, the direct proof of Gb as anti-parasitic molecule as well as a concept for its potential therapeutic use against malarial infections is provided. Therefore, a soluble Gb was produced in HEK293 cells and purified by Ni-NTA IMAC from the culture supernatant as described before (Losasso, Schiffer et al. 2012). Gb was expressed as EGb, meaning fused to an N-terminal enterokinase cleavage site to suppress enzymatic activity and therewith to suppress induction of apoptosis in the expressing cells. After activation by digest using 0.02 U recombinant enterokinase/μg protein as described before (Losasso, Schiffer et al. 2012), the susceptibility of *P. falciparum* 3D7A towards active and inactive Gb was tested in a 72-h assay starting at synchronized ring-stage (Kreidenweiss, Kremsner et al. 2008) (FIG. 3). Here, parasite growth was specifically inhibited by active Gb with a half maximal inhibitory concentration (IC50-value) of 1590 nM (CI: 1197-2112 nM)) (calculated by Hill equation using GraphPad Prism v5) whereas the undigested protein, meaning inactive form of EGb, showed no inhibition.

Example 2: Specific Targeting of the Merozoite Membrane

A strategy to more directly target Gb to the parasite was developed to reduce the amount of applied Gb. Targeted toxin-delivery via the parasite transferrin receptor has been presented by Surolia et al. several years ago (Surolia and Misquith 1996, Surolia 2000). While some authors claimed to have identified and characterized this plasmodial receptor (Haldar, Henderson et al. 1986, Rodriguez and Jungery 1986), others, however, argue unspecific iron uptake by the parasite and the identification of this receptor remains elusive (Clark, Fisher et al. 2013). Therefore, there is a need for a definite specific target. Promising possible targets are merozoite surface proteins (MSPs). MSP1, 2, 4 and 8 bear GPI anchors which prevent them from being shedded during merozoite invasion. They contain C-terminal, GPI anchor-adjacent, immunogenic EGF-like domains which serve as ideal target for specific antibodies (Blackman, Heidrich et al. 1990, Marshall, Silva et al. 1997, Drew, Sanders et al. 2005, Garcia, Puentes et al. 2007). Recently, it has been shown that MSP4 is carried into the newly infected erythrocyte without remarkable processing and remains there up to 5 h (Boyle, Langer et al. 2013). This makes MSP4-specific antibody molecules attractive candidates to guide Gb into the infected erythrocyte.

For this purpose the V-gene sequences was isolated from an MSP4 specific murine hybridoma cell line named 2.44. The VH-gene sequence was cloned in a binary plant expression vector encoding for a human IgG1 constant domain (allotype m17.1) via AgeI and SalI. The VL-gene sequence was cloned into a binary plant expression vector encoding for a human kappal constant domain (allotype Km3) via AgeI and BsiWI. Electrocompetent Rhizobium radiobacter (strain GV3101 PMP90RK) were separately transformed with these vectors and were used for the infiltration of Nicotiana benthamiana plants to transiently express the antibody as full-size recombinant chimeric 2.44IgG1 as described before (Fendel et al., Pat. No. WO2014020062). The specificity for MSP4 of this recombinant chimeric full-size antibody 2.44IgG1 was assessed in an enzyme-linked immunosorbent assay (ELISA) and immunofluorescence assay (IFA).

The ELISA was performed on EIA plates coated with recombinant MSP4. Serial dilutions of recombinant chimeric antibody 2.44IgG1 were added and subsequently detected using a goat anti-human IgG antibody (Jackson Immuno-Research, Fc-specific and conjugated to a peroxidase). The reactions were visualized with TMB (Invitrogen) for 5 min and then the reaction was stopped with 1 M HCl. The absorbance was read at 450 nm. The IFA was performed by fixation of mature *P. falciparum* schizonts on microiscopy slides using 100% methanol at −20° C. 50 µg/ml2.44IgG1 were probed using a goat anti-human IgGAlexaFluor®647 secondary antibody. Costaining was performed with a polyclonal rabbit anti-AMA1 antibody (BG98) which was visualized with a goat anti-rabbitAlexaFluor®488 secondary antibody. Parasite nuclei were stained with 10 µg/ml Hoechst33342.

Example 3: Anti-Parasitic Activity of Recombinant Anti-Parasitic Fusion Protein on PF 3D7 and PFK1

For targeted delivery of Gb, we generated a scFv from the 2.44IgG1 antibody sequence by SOE-PCR using specifically designed primers which enable subsequent cloning via SfiI and NotI
(FORWARD PRIMER: AACAACGGCCCAGCCGGC-CATGGCCGATGTGCAGCTTCAGGAGTCGGG (SEQ ID NO. 11)),
REVERSE PRIMER: ATGGTGGGCGGCCGCTTTT-ATTTCCAACTTTGTCCCC (SEQ ID NO. 12)).

Between the V-gene segments, a glycine-serine linker was incorporated
(FORWARD PRIMER: GGAGCCGCCGCCGCCAGAAC-CACCACCACCAGAACCACCACCACCT GAGGA-GACGGTGACCGTGGTCCC (SEQ ID NO. 13)),
REVERSE PRIMER: GGCGGCGGCGGCTCCGGTG-GTGGTGGATCCGAAATTGTCCTCACCCAGTCTC C (SEQ ID NO. 14)).

The scFv was genetically fused to the SerpinB9-resistant EGbR201K-mutant flanked with XbaI and BlpI restriction sites. The protein sequence of the final expression construct including its motifs and tags is shown in FIG. 4. The expression cassette was cloned via XbaI and NotI into a pTT5SH8Q2 expression vector (based on pTT, (Durocher, Perret et al. 2002)). The fusion protein was expressed in HEK293-6E cells as described before (Durocher, Perret et al. 2002) and purified by NiNTA IMAC as described in example 1, but using binding and washing buffers devoid of imidazole. As controls, the two unrelated scFvs H22 (specific for CD64) (Stahnke, Thepen et al. 2008) and Ki4 (specific for CD30) (Schiffer, Hansen et al. 2013) fused to EGbR201K were equally produced and purified.

After activation of EGb-scFv fusion proteins by enterokinase digest as described in example 1, fusion proteins were used in a 48-h drug susceptibility assay. The assay duration was shortened to one replication cycle because only the co-importing step was necessary for the assessment. Proteins were added to synchronous schizont-stage parasites at a parasitemia of 0.05% and a final hematocrit of 1.5% in a total volume of 50 µl in 96-well half-area microtiter cell culture plates for 48 h. Parasite growth was assessed by ELISA quantifying PfHRP2 as described before (Noedl, Bronnert et al. 2005).

To control the dependence on the co-import of Gb-2.44 after schizont rupture into the newly infected erythrocyte along with the merozoite, a 30-h drug susceptibility assay was performed. Here, fusion proteins were added to synchronous ring-stage parasites at 0.2% parasitemia and 1.5% hematocrit and incubated for 30 h until mature schizonts were developed. The assay was analysed by PfHRP2-ELISA as described before (Noedl, Bronnert et al. 2005).

The results showed that Gb-2.44 had a 5-8-fold decreased half maximal inhibitory concentration (IC50-value) of 176 nM (CI: 154-202 nM) in comparison to Gb, Gb-H22 and Gb-Ki4, which inhibited parasites with higher IC50-values around 1000 nM (FIG. 4 A). Undigested, meaning inactive, controls (EGb-2.44, EGb-H22, EGb-Ki4 and EGb; data not shown) as well as the full-size antibody 2.44IgG1 did not have any effect on parasite growth in relevant concentrations. Similar 48-h drug susceptibility assays were performed on the multi-drug resistant strain *P. falciparum* K1 (FIG. 4 B). In this assay, similar results were obtained. The PfMSP4-specific Gb-2.44 again had a decreased IC50-value of 247 nM (CI: 200-303 nM), thereby again being more effective than the *P. falciparum*-unrelated Gb-Ki4. Gb-Ki4 showed an IC50-value above 800 nM. In the 30-h drug susceptibility assay, all tested samples (Gb-2.44, Gb-H22 and unfused Gb) showed similar IC50-values >1 µM (FIG. 5).

Taken together, we demonstrate that Gb is a molecule with antiparasitic activity in example 1. With our isolated *P. falciparum* merozoite specific antibody (example 2), we were able to decrease the IC50-value by 5-8-fold (example 3). Furthermore, the necessity of the co-importing step was also proven in example 3 by the usage of a 30-h control drug susceptibility assay. These data in summary clearly demonstrate the applicability of Gb and Gb-scFv fusion proteins as antiparasitic agents.

REFERENCES

The contents of all cited references, including literature references, issued patents, and published patent applications, as cited throughout this application are hereby expressly incorporated by reference.

Ausubel, F. M. (1992). Current Protocols in Molecular Biology. New York, John Wiley & Sons.

Blackman, M. J., H. G. Heidrich, S. Donachie, J. S. McBride and A. A. Holder (1990). "A single fragment of a malaria merozoite surface protein remains on the parasite during red cell invasion and is the target of invasion-inhibiting antibodies." *J Exp Med* 172 (1): 379-382.

Bottger, E., G. Multhoff, J. F. Kun and M. Esen (2012). "*Plasmodium falciparum*-infected erythrocytes induce granzyme B by NK cells through expression of host-Hsp70." *PLoS One* 7(3): e33774.

Boyle, M. J., C. Langer, J. A. Chan, A. N. Hodder, R. L. Coppel, R. F. Anders and J. G. Beeson (2014). "Sequential processing of merozoite surface proteins during and after erythrocyte invasion by *Plasmodium falciparum*." *Infect Immun* 82(3):924-936.

Clark, M., N. C. Fisher, R. Kasthuri and C. Cerami Hand (2013). "Parasite maturation and host serum iron influence the labile iron pool of erythrocyte stage *Plasmodium falciparum*." *Br J Haematol* 161(2): 262-269.

Drew, D. R., P. R. Sanders and B. S. Crabb (2005). "*Plasmodium falciparum* merozoite surface protein 8 is a ring-stage membrane protein that localizes to the parasitophorous vacuole of infected erythrocytes." *Infect Immun* 73(7): 3912-3922.

Durocher, Y., S. Perret and A. Kamen (2002). "High-level and high-throughput recombinant protein production by transient transfection of suspension-growing human 293-EBNA1 cells." *Nucleic Acids Res* 30(2): E9.

Gardner, M. J., N. Hall, E. Fung, O. White, M. Berriman, R. W. Hyman, J. M. Carlton, A. Pain, K. E. Nelson, S. Bowman and et al. (2002). "Genome sequence of the human malaria parasite *Plasmodium falciparum*." *Nature* 419(6906): 498-511.

Garcia, J. E., A. Puentes and M. E. Patarroyo (2006). "Developmental biology of sporozoite-host interactions in *Plasmodium falciparum* malaria: implications for vaccine design." *Clin Microbiol Rev* 19(4): 686-707.

Garcia, Y., A. Puentes, H. Curtidor, G. Cifuentes, C. Reyes, J. Barreto, A. Moreno and M. E. Patarroyo (2007). "Identifying merozoite surface protein 4 and merozoite surface protein 7 *Plasmodium falciparum* protein family members specifically binding to human erythrocytes suggests a new malarial parasite-redundant survival mechanism." *J Med Chem* 50(23): 5665-5675.

Haldar, K., C. L. Henderson and G. A. Cross (1986). "Identification of the parasite transferrin receptor of *Plasmodium falciparum*-infected erythrocytes and its acylation via 1,2-diacyl-sn-glycerol." *Proc Natl Acad Sci USA* 83(22): 8565-8569.

Hermsen, C. C., Y. Konijnenberg, L. Mulder, C. Loe, M. van Deuren, J. W. van der Meer, G. J. van Mierlo, W. M. Eling, C. E. Hack and R. W. Sauerwein (2003). "Circulating concentrations of soluble granzyme A and B increase during natural and experimental *Plasmodium falciparum* infections." *Clin Exp Immunol* 132(3): 467-472.

Hiller N. L., S. Bhattacharjee, C. van Ooij, K. Liolios, T. Harrison, C. Lopez-Estratio and K. Haldar (2004). "A host-targeting signal in virulence proteins reveals a secretome in malarial infection." *Science* 306(5703): 1934-1937.

Huston, J. S., D. Levinson, M. Mudgett-Hunter, M. S. Tai, J. Novotny, M. N. Margolies, R. J. Ridge, R. E. Bruccoleri, E. Haber, R. Crea and et al. (1988). "Protein engineering of antibody binding sites: recovery of specific activity in an anti-digoxin single-chain Fv analogue produced in *Escherichia coli*." *Proc Natl Acad Sci USA* 85(16): 5879-5883.

Kabat, E. A. (1987). Sequences of proteins of immunological interest. Bethesda, U.S. Dept. of Health and Human Services, Public Health Service, National Institutes of Health.

Kreidenweiss, A., P. G. Kremsner and B. Mordmuller (2008). "Comprehensive study of proteasome inhibitors against *Plasmodium falciparum* laboratory strains and field isolates from Gabon." *Malar J* 7: 187.

Losasso, V., S. Schiffer, S. Barth and P. Carloni (2012). "Design of human granzyme B variants resistant to serpin B9." *Proteins* 80(11): 2514-2522.

Marshall, V. M., A. Silva, M. Foley, S. Cranmer, L. Wang, D. J. McColl, D. J. Kemp and R. L. Coppel (1997). "A second merozoite surface protein (MSP-4) of *Plasmodium falciparum* that contains an epidermal growth factor-like domain." *Infect Immun* 65(11): 4460-4467.

Marti, M., R. T. Good, M. Rug, E. Knuepfer and A. F. Cowman (2004). "Targeting malaria virulence and remodeling proteins to the host erythrocyte." *Science* 306(5703): 1930-3.

Noedl, H., J. Bronnert, K. Yingyuen, B. Attlmayr, H. Kollaritsch and M. Fukuda (2005). "Simple histidine-rich protein 2 double-site sandwich enzyme-linked immunosorbent assay for use in malaria drug sensitivity testing." *Antimicrob Agents Chemother* 49(8): 3575-3577.

Nussenzweig, V. and R. S. Nussenzweig (1989). "Circumsporozoite proteins of malaria parasites." *Bull Mem Acad R Med Belg* 144(11): 493-504.

Paul, W. E. (1993). *Fundamental immunology*. New York, Raven Press.

Rodriguez, M. H. and M. Jungery (1986). "A protein on *Plasmodium falciparum*-infected erythrocytes functions as a transferrin receptor." *Nature* 324(6095): 388-391.

Rousalova, I. and E. Krepela (2010). "Granzyme B-induced apoptosis in cancer cells and its regulation (review)." *Int J Oncol* 37(6): 1361-1378.

Sambrook, J., T. Maniatis and E. F. Fritsch (1989). *Molecular cloning: A laboratory manual*. Cold Spring Harbor, N.Y., Cold Spring Harbor Laboratory Press.

Sambrook, J. and D. W. Russell (2001). *Molecular cloning: A laboratory manual*. Cold Spring Harbor, N.Y., Cold Spring Harbor Labratory Press.

Schiffer, S., H. P. Hansen, G. Hehmann-Titt, M. Huhn, R. Fischer, S. Barth and T. Thepen (2013). "Efficacy of an adapted granzyme B-based anti-CD30 cytolytic fusion protein against PI-9-positive classical Hodgkin lymphoma cells in a murine model." *Blood Cancer J* 3: e106.

Sim, B. K., T. Toyoshima, J. D. Haynes and M. Aikawa (1992). "Localization of the 175-kilodalton erythrocyte binding antigen in micronemes of *Plasmodium falciparum* merozoites." *Mol Biochem Parasitol* 51(1): 157-159.

Smith J. D. and A. G. Craig (2005). "The surface of the *Plasmodium falciparum*-infected erythrocyte." *Curr Issues Mol Biol* 7(1): 81-93.

Stahnke, B., T. Thepen, M. Stocker, R. Rosinke, E. Jost, R. Fischer, M. K. Tur and S. Barth (2008). "Granzyme B-H22(scFv), a human immunotoxin targeting CD64 in acute myeloid leukemia of monocytic subtypes." *Mol Cancer Ther* 7(9): 2924-2932.

Surolia, N. (2000). "Receptor-mediated targeting of toxins to intraerythrocytic parasite *Plasmodium falciparum*." *Adv Drug Deliv Rev* 41(2): 163-170.

Surolia, N. and S. Misquith (1996). "Cell surface receptor directed targeting of toxin to human malaria parasite, *Plasmodium falciparum*." *FEBS Lett* 396(1): 57-61.

Tarun A. S., X. Peng, R. F. Dumpit, Y. Ogata, H. Silva-Rivera, N. Camargo, T. M. Daly, L. W. Bergman and S. H. Kappe (2008). "A combined transcriptome and proteome survey of malaria parasite liver stages." *Proc Natl Acad Sci USA* 105(1):305-310.

Wasmuth, J., J. Daub, J. M. Peregrin-Alvarez, C. A. Finney and J. Parkinson (2009). "The origins of apicomplexan sequence innovation." *Genome Res* 19(7): 1202-1213.

What is claimed is:

1. A complex comprising at least one component A and at least one component B, characterized in that component A is an antibody or antibody fragment that has a binding activity for cellular surface structures presented on the surface of a parasite of the genus *Plasmodium* and component B is a variant of human granzyme B having direct anti-parasitic activity, wherein the cellular surface structure is selected from the group consisting of cell traversal protein for ookinetes and sporozoites (CelTos), circumsporozoite protein (CSP), Exported Protein 1 (EXPO, Merozoite surface protein 1 (MSP1), Merozoite surface protein 2 (MSP2), Merozoite surface protein 3 (MSP3), Merozoite surface protein 4 (MSP4), Merozoite surface protein 5 (MSPS), Merozoite surface protein 7 (MSP7), Merozoite surface protein 8 (MSPS), Merozoite surface protein 9 (MSPS), Merozoite surface protein 10 (MSP10), Merozoite-specific thrombospondin-related anonymous protein (mTRAP), *Plasmodium falciparum* 6-cys protein (Pf38), Reticulocyte binding protein homologue 1 (Rh1), Reticulocyte binding protein 2 homolog a (Rh2a), Reticulocyte binding protein 2 homologue b (Rh2b), Reticulocyte binding protein homologue 4 (Rh4), Reticulocyte binding protein homologue 5 (Rh5), Rh5 interacting protein (Ripr), rhoptry neck protein 2 (RON2), rhoptry neck protein 4 (RON4), rhoptry neck protein 5 (RON5), *Plasmodium falciparum* rhoptry neck protein 6 (PfRON6), Thrombospondin-related apical membrane protein (TRAMP), Apical membrane antigen 1 (AMA1), Glutamine rich protein (GLURP), High Molecular Weight Rhoptry Protein-2 (RhopH2) and High Molecular Weight Rhoptry Protein-3 (RhopH3), and wherein the variant of human granzyme B comprises an amino acid sequence selected from the group consisting of SEQ ID NO: 7, SEQ ID NO: 8, SEQ ID NO:9, and SEQ ID NO: 10.

2. The complex according to claim 1, wherein the parasite of the genus *Plasmodium* is selected from the group consisting of *P. falciparum, P. vivax, P. ovate, P. knowlesi*, and *P. malariae*.

3. The complex according to claim 1, wherein the parasitic cellular surface structures are presented in the pre-erythrocytic stage and/or the blood stage.

4. The complex according to claim 1, wherein the antibody or antibody fragment is selected from the group consisting of an Fab, a scFv, a single domain, a bis scFv, an Fab$_2$, an Fab$_3$, a minibody, a diabody, a triabody, a tetrabody and a tandab.

5. The complex according to claim 4, wherein the scFv is specific for an epidermal growth-factor-like domain of merozoite surface protein 4 (MSP4).

6. The complex according to claim 1, wherein the complex is a fusion protein.

7. The complex according to claim 1 containing one or more supplementary components S in addition to said components A and B, wherein component S is selected from the group consisting of an inducible promoter capable of regulating expression, a leader sequence capable of controlling protein biosynthesis, a Histadine (HIS) tag, an affinity tag, and a translocation domain amphipathic sequence capable of translocating a fusion protein into a target cell.

8. A complex comprising the amino acid sequence of SEQ ID NO: 1.

9. The complex according to claim 4, wherein component A is the single chain variable fragment (scFv).

10. A pharmaceutical composition comprising a complex according to claim 1 in combination with a pharmacologically acceptable carrier, diluent, stabilizer or formulation.

11. A nucleic acid molecule coding for the fusion protein according to claim 6.

12. A vector carrying the nucleic acid molecule according to claim 11.

13. A cell transfected with the vector according to claim 12.

14. A method for preparing a complex, wherein the method comprises culturing the cell according to claim 13 and isolating the complex from the cell culture.

* * * * *

SEQUENCE LISTING

```
<160> NUMBER OF SEQ ID NOS: 14

<210> SEQ ID NO 1
<211> LENGTH: 529
<212> TYPE: PRT
<213> ORGANISM: Artificial Sequence
<220> FEATURE:
<223> OTHER INFORMATION: Synthetic Construct

<400> SEQUENCE: 1

Ser Arg His Ile Asp Asp Asp Lys Ile Ile Gly Gly His Glu Ala
1               5                   10                  15

Lys Pro His Ser Arg Pro Tyr Met Ala Phe Leu Met Ile Trp Asp Gln
            20                  25                  30

Lys Ser Leu Lys Arg Cys Gly Gly Phe Leu Ile Arg Asp Asp Phe Val
        35                  40                  45

Leu Thr Ala Ala His Cys Trp Gly Ser Ser Ile Asn Val Thr Leu Gly
    50                  55                  60

Ala His Asn Ile Lys Glu Gln Glu Pro Thr Gln Gln Phe Ile Pro Val
65                  70                  75                  80

Lys Arg Ala Ile Pro His Pro Ala Tyr Asn Pro Lys Asn Phe Ser Asn
                85                  90                  95

Asp Ile Met Leu Leu Gln Leu Glu Arg Lys Ala Lys Arg Thr Arg Ala
            100                 105                 110

Val Gln Pro Leu Arg Leu Pro Ser Asn Lys Ala Gln Val Lys Pro Gly
        115                 120                 125

Gln Thr Cys Ser Val Ala Gly Trp Gly Gln Thr Ala Pro Leu Gly Lys
    130                 135                 140

His Ser His Thr Leu Gln Glu Val Lys Met Thr Val Gln Glu Asp Arg
145                 150                 155                 160

Lys Cys Glu Ser Asp Leu Arg His Tyr Tyr Asp Ser Thr Ile Glu Leu
                165                 170                 175

Cys Val Gly Asp Pro Glu Ile Lys Lys Thr Ser Phe Lys Gly Asp Ser
            180                 185                 190

Gly Gly Pro Leu Val Cys Asn Lys Val Ala Gln Gly Ile Val Ser Tyr
        195                 200                 205

Gly Lys Asn Asn Gly Met Pro Pro Arg Ala Cys Thr Lys Val Ser Ser
    210                 215                 220

Phe Val His Trp Ile Lys Lys Thr Met Lys Arg Tyr Ala Glu His Glu
225                 230                 235                 240

Gly Asp Ala Ala Gln Pro Ala Met Ala Asp Val Gln Leu Gln Glu Ser
                245                 250                 255

Gly Pro Gly Leu Val Lys Pro Ser Gln Ser Leu Ser Leu Thr Cys Thr
            260                 265                 270

Val Thr Gly Tyr Ser Ile Thr Ser Asp Phe Ala Trp Asn Trp Ile Arg
        275                 280                 285
```

-continued

```
Gln Phe Pro Gly Asn Arg Leu Glu Trp Met Gly Tyr Met Gly Tyr Thr
    290                 295                 300
Gly Ser Thr Ser Tyr Asn Pro Ser Leu Arg Gly Arg Ile Ser Ile Thr
305                 310                 315                 320
Arg Asp Thr Ser Lys Asn Gln Phe Phe Leu Gln Leu Asn Ser Val Thr
                325                 330                 335
Thr Glu Asp Thr Ala Thr Tyr Tyr Cys Ala Arg Gly Asp Tyr Tyr Gly
            340                 345                 350
Ser Arg Gly Tyr Phe Asp Val Trp Gly Ala Gly Thr Thr Val Thr Val
        355                 360                 365
Ser Ser Gly Gly Gly Gly Ser Gly Gly Gly Ser Ser Gly Gly Gly
370                 375                 380
Ser Gly Gly Gly Ser Glu Ile Val Leu Thr Gln Ser Pro Ala Leu
385                 390                 395                 400
Met Ala Ala Ser Pro Gly Glu Lys Val Thr Ile Thr Cys Ser Val Ser
                405                 410                 415
Ser Ser Ile Arg Ser Ser Asn Leu His Trp Tyr Gln Gln Lys Ser Asp
            420                 425                 430
Thr Ser Pro Lys Pro Trp Ile Tyr Gly Thr Ser Asn Leu Ala Ser Gly
        435                 440                 445
Val Pro Val Arg Phe Ser Gly Ser Gly Ser Gly Thr Ser Tyr Ser Leu
450                 455                 460
Thr Ile Ser Thr Met Glu Ala Glu Asp Ala Ala Thr Tyr Tyr Cys Gln
465                 470                 475                 480
Gln Trp Ser Ser Tyr Pro Phe Thr Phe Gly Ser Gly Thr Lys Leu Glu
                485                 490                 495
Ile Lys Ala Ala Ala Asn Ser Ser Leu Gly Ser Gly Trp Ser His Pro
            500                 505                 510
Gln Phe Glu Lys Thr Gly His His His His His His Gly Gly
        515                 520                 525
Gln

<210> SEQ ID NO 2
<211> LENGTH: 227
<212> TYPE: PRT
<213> ORGANISM: Homo sapiens

<400> SEQUENCE: 2

Ile Ile Gly Gly His Val Ala Lys Pro His Ser Arg Pro Tyr Met Ala
1               5                   10                  15
Tyr Leu Met Ile Trp Asp Gln Lys Ser Leu Lys Arg Cys Gly Gly Phe
            20                  25                  30
Leu Ile Arg Asp Asp Phe Val Leu Thr Ala Ala His Cys Trp Gly Ser
        35                  40                  45
Ser Ile Asn Val Thr Leu Gly Ala His Asn Ile Lys Glu Gln Glu Pro
    50                  55                  60
Thr Gln Gln Phe Ile Pro Val Lys Arg Ala Ile Pro His Pro Ala Tyr
65                  70                  75                  80
Asn Pro Lys Asn Phe Ser Asn Asp Ile Met Leu Leu Gln Leu Glu Arg
                85                  90                  95
Lys Ala Lys Arg Thr Arg Ala Val Gln Pro Leu Arg Leu Pro Ser Asn
            100                 105                 110
Lys Ala Gln Val Lys Pro Gly Gln Thr Cys Ser Val Ala Gly Trp Gly
        115                 120                 125
```

```
        Gln Thr Ala Pro Leu Gly Lys His Ser His Thr Leu Gln Glu Val Lys
            130                 135                 140

Met Thr Val Gln Glu Asp Arg Lys Cys Glu Ser Asp Leu Arg His Tyr
        145                 150                 155                 160

Tyr Asp Ser Thr Ile Glu Leu Cys Val Gly Asp Pro Glu Ile Lys Lys
                        165                 170                 175

Thr Ser Phe Lys Gly Asp Ser Gly Gly Pro Leu Val Cys Asn Lys Val
                    180                 185                 190

Ala Gln Gly Ile Val Ser Tyr Gly Arg Asn Asn Gly Met Pro Pro Arg
                195                 200                 205

Ala Cys Thr Lys Val Ser Ser Phe Val His Trp Ile Lys Lys Thr Met
            210                 215                 220

Lys Arg Tyr
        225

<210> SEQ ID NO 3
<211> LENGTH: 681
<212> TYPE: DNA
<213> ORGANISM: Homo sapiens

<400> SEQUENCE: 3
atcatcgggg gacatgaggc caagccccac tcccgcccct acatggcttt tcttatgatc      60
tgggatcaga agtctctgaa gaggtgcggt ggcttcctga tacgagacga cttcgtgctg     120
acagctgctc actgttgggg aagctccata aatgtcacct gggggcccca caatatcaag     180
gaacaggagc cgacccagca gtttatccct gtgaaaagag ccatccccca tccagcctat     240
aatcctaaga acttctccaa tgacatcatg ctactgcagc tggagagaaa ggccaagcgg     300
accagagctg tgcagcccct caggctacct agcaacaagg cccaggtgaa gccagggcag     360
acatgcagtg tggccggctg ggggcagacg gccccctgg aaaacactc acacacacta      420 caagaggtga agatgacagt gcaggaagat cgaaagtgcg aatctgactt acgccattat     480
tacgacagta ccattgagtt gtgcgtgggg gacccagaga ttaaaaagac ttccttttaag   540 ggggactctg gaggccctct tgtgtgtaac aaggtggccc agggcattgt ctcctatgga    600
cgaaacaatg gcatgcctcc acgagcctgc accaaagtct caagctttgt acactggata    660
aagaaaacca tgaaacgcta c                                              681

<210> SEQ ID NO 4
<211> LENGTH: 681
<212> TYPE: DNA
<213> ORGANISM: Homo sapiens

<400> SEQUENCE: 4
atcatcgggg gacatgaggc caagccccac tcccgcccct acatggcttt tcttatgatc      60
tgggatcaga agtctctgaa gaagtgcggt ggcttcctga tacgagacga cttcgtgctg     120
acagctgctc actgttgggg aagctccata aatgtcacct gggggcccca caatatcaag     180
gaacaggagc cgacccagca gtttatccct gtgaaaagag ccatccccca tccagcctat     240
aatcctaaga acttctccaa tgacatcatg ctactgcagc tggagagaaa ggccaagcgg     300
accagagctg tgcagcccct caggctacct agcaacaagg cccaggtgaa gccagggcag     360
acatgcagtg tggccggctg ggggcagacg gccccctgg aaaacactc acacacacta      420 caagaggtga agatgacagt gcaggaagat cgaaagtgcg aatctgactt acgccattat     480
tacgacagta ccattgagtt gtgcgtgggg gacccagaga ttaaaaagac ttccttttaag   540
```

```
ggggactctg gaggccctct tgtgtgtaac aaggtggccc agggcattgt ctcctatgga      600
cgaaacaatg gcatgcctcc acgagcctgc accaaagtct caagctttgt acactggata      660
aagaaaacca tgaaacgcta c                                                681

<210> SEQ ID NO 5
<211> LENGTH: 681
<212> TYPE: DNA
<213> ORGANISM: Homo sapiens

<400> SEQUENCE: 5
atcatcgggg acatgaggc caagccccac tcccgcccct acatggcttt tcttatgatc        60
tgggatcaga agtctctgaa gaggtgcggt ggcttcctga tacgagacga cttcgtgctg      120
acagctgctc actgttgggg aagctccata aatgtcacct ggggggccca caatatcaag      180
gaacaggagc cgacccagca gtttatccct gtgaaaagag ccatccccca tccagcctat      240
aatcctaaga acttctccaa tgacatcatg ctactgcagc tggagagaaa ggccaagcgg      300
accagagctg tgcagcccct caggctacct agcaacaagg cccaggtgaa gccagggcag      360
acatgcagtg tggccggctg ggggcagacg gccccctgg aaaacactc acacacacta       420 caagaggtga agatgacagt gcaggaagat cgaaagtgcg aatctgactt acgccattat      480
tacgacagta ccattgagtt gtgcgtgggg gacccagaga ttaaaaagac ttccttaag       540 ggggactctg gaggccctct tgtgtgtaac aaggtggccc agggcattgt ctcctatgga      600
gcaaacaatg gcatgcctcc acgagcctgc accaaagtct caagctttgt acactggata      660
aagaaaacca tgaaacgcta c                                                681

<210> SEQ ID NO 6
<211> LENGTH: 681
<212> TYPE: DNA
<213> ORGANISM: Homo sapiens

<400> SEQUENCE: 6
atcatcgggg acatgaggc caagccccac tcccgcccct acatggcttt tcttatgatc        60
tgggatcaga agtctctgaa gaggtgcggt ggcttcctga tacgagacga cttcgtgctg      120
acagctgctc actgttgggg aagctccata aatgtcacct ggggggccca caatatcaag      180
gaacaggagc cgacccagca gtttatccct gtgaaaagag ccatccccca tccagcctat      240
aatcctaaga acttctccaa tgacatcatg ctactgcagc tggagagaaa ggccaagcgg      300
accagagctg tgcagcccct caggctacct agcaacaagg cccaggtgaa gccagggcag      360
acatgcagtg tggccggctg ggggcagacg gccccctgg aaaacactc acacacacta       420 caagaggtga agatgacagt gcaggaagat cgaaagtgcg aatctgactt acgccattat      480
tacgacagta ccattgagtt gtgcgtgggg gacccagaga ttaaaaagac ttccttaag       540 ggggactctg gaggccctct tgtgtgtaac aaggtggccc agggcattgt ctcctatgga      600
aagaacaatg gcatgcctcc acgagcctgc accaaagtct caagctttgt acactggata      660
aagaaaacca tgaaacgcta c                                                681

<210> SEQ ID NO 7
<211> LENGTH: 227
<212> TYPE: PRT
<213> ORGANISM: Homo sapiens
```

<400> SEQUENCE: 7

```
Ile Ile Gly Gly His Val Ala Lys Pro His Ser Arg Pro Tyr Met Ala
1               5                   10                  15

Tyr Leu Met Ile Trp Asp Gln Lys Ser Leu Lys Ala Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
    130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Gly Pro Leu Val Cys Asn Lys Val
            180                 185                 190

Ala Gln Gly Ile Val Ser Tyr Gly Arg Asn Asn Gly Met Pro Pro Arg
        195                 200                 205

Ala Cys Thr Lys Val Ser Ser Phe Val His Trp Ile Lys Lys Thr Met
    210                 215                 220

Lys Arg Tyr
225
```

<210> SEQ ID NO 8
<211> LENGTH: 227
<212> TYPE: PRT
<213> ORGANISM: Homo sapiens

<400> SEQUENCE: 8

```
Ile Ile Gly Gly His Val Ala Lys Pro His Ser Arg Pro Tyr Met Ala
1               5                   10                  15

Tyr Leu Met Ile Trp Asp Gln Lys Ser Leu Lys Lys Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
    50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125
```

```
Gln Thr Ala Pro Leu Gly Lys His Ser His Thr Leu Gln Glu Val Lys
        130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Pro Leu Val Cys Asn Lys Val
                180                 185                 190

Ala Gln Gly Ile Val Ser Tyr Gly Arg Asn Asn Gly Met Pro Pro Arg
            195                 200                 205

Ala Cys Thr Lys Val Ser Ser Phe Val His Trp Ile Lys Lys Thr Met
        210                 215                 220

Lys Arg Tyr
225

<210> SEQ ID NO 9
<211> LENGTH: 227
<212> TYPE: PRT
<213> ORGANISM: Homo sapiens

<400> SEQUENCE: 9

Ile Ile Gly Gly His Val Ala Lys Pro His Ser Arg Pro Tyr Met Ala
1               5                   10                  15

Tyr Leu Met Ile Trp Asp Gln Lys Ser Leu Lys Arg Cys Gly Gly Phe
            20                  25                  30

Leu Ile Arg Asp Asp Phe Val Leu Thr Ala Ala His Cys Trp Gly Ser
        35                  40                  45

Ser Ile Asn Val Thr Leu Gly Ala His Asn Ile Lys Glu Gln Glu Pro
50                  55                  60

Thr Gln Gln Phe Ile Pro Val Lys Arg Ala Ile Pro His Pro Ala Tyr
65                  70                  75                  80

Asn Pro Lys Asn Phe Ser Asn Asp Ile Met Leu Leu Gln Leu Glu Arg
                85                  90                  95

Lys Ala Lys Arg Thr Arg Ala Val Gln Pro Leu Arg Leu Pro Ser Asn
            100                 105                 110

Lys Ala Gln Val Lys Pro Gly Gln Thr Cys Ser Val Ala Gly Trp Gly
        115                 120                 125

Gln Thr Ala Pro Leu Gly Lys His Ser His Thr Leu Gln Glu Val Lys
        130                 135                 140

Met Thr Val Gln Glu Asp Arg Lys Cys Glu Ser Asp Leu Arg His Tyr
145                 150                 155                 160

Tyr Asp Ser Thr Ile Glu Leu Cys Val Gly Asp Pro Glu Ile Lys Lys
                165                 170                 175

Thr Ser Phe Lys Gly Asp Ser Gly Pro Leu Val Cys Asn Lys Val
                180                 185                 190

Ala Gln Gly Ile Val Ser Tyr Gly Ala Asn Asn Gly Met Pro Pro Arg
            195                 200                 205

Ala Cys Thr Lys Val Ser Ser Phe Val His Trp Ile Lys Lys Thr Met
        210                 215                 220

Lys Arg Tyr
225

<210> SEQ ID NO 10
<211> LENGTH: 227
<212> TYPE: PRT
<213> ORGANISM: Homo sapiens
```

-continued

<400> SEQUENCE: 10

Ile Ile Gly Gly His Val Ala Lys Pro His Ser Arg Pro Tyr Met Ala
1               5                   10                  15
Tyr Leu Met Ile Trp Asp Gln Lys Ser Leu Lys Arg Cys Gly Gly Phe
            20                  25                  30
Leu Ile Arg Asp Asp Phe Val Leu Thr Ala Ala His Cys Trp Gly Ser
        35                  40                  45
Ser Ile Asn Val Thr Leu Gly Ala His Asn Ile Lys Glu Gln Glu Pro
    50                  55                  60
Thr Gln Gln Phe Ile Pro Val Lys Arg Ala Ile Pro His Pro Ala Tyr
65                  70                  75                  80
Asn Pro Lys Asn Phe Ser Asn Asp Ile Met Leu Leu Gln Leu Glu Arg
                85                  90                  95
Lys Ala Lys Arg Thr Arg Ala Val Gln Pro Leu Arg Leu Pro Ser Asn
            100                 105                 110
Lys Ala Gln Val Lys Pro Gly Gln Thr Cys Ser Val Ala Gly Trp Gly
        115                 120                 125
Gln Thr Ala Pro Leu Gly Lys His Ser His Thr Leu Gln Glu Val Lys
    130                 135                 140
Met Thr Val Gln Glu Asp Arg Lys Cys Glu Ser Asp Leu Arg His Tyr
145                 150                 155                 160
Tyr Asp Ser Thr Ile Glu Leu Cys Val Gly Asp Pro Glu Ile Lys Lys
                165                 170                 175
Thr Ser Phe Lys Gly Asp Ser Gly Gly Pro Leu Val Cys Asn Lys Val
            180                 185                 190
Ala Gln Gly Ile Val Ser Tyr Gly Lys Asn Asn Gly Met Pro Pro Arg
        195                 200                 205
Ala Cys Thr Lys Val Ser Ser Phe Val His Trp Ile Lys Lys Thr Met
    210                 215                 220
Lys Arg Tyr
225

<210> SEQ ID NO 11
<211> LENGTH: 48
<212> TYPE: DNA
<213> ORGANISM: ARTIFICIAL SEQUENCE
<220> FEATURE:
<223> OTHER INFORMATION: SYNTHETIC SEQUENCE

<400> SEQUENCE: 11
aacaacggcc cagccggcca tggccgatgt gcagcttcag gagtcggg                48

<210> SEQ ID NO 12
<211> LENGTH: 37
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 12
atggtgggcg gccgctttta tttccaactt tgtcccc                             37

<210> SEQ ID NO 13
<211> LENGTH: 69
<212> TYPE: DNA
<213> ORGANISM: ARTIFICIAL SEQUENCE
<220> FEATURE:
<223> OTHER INFORMATION: SYNTHETIC CONSTRUCT

```
<400> SEQUENCE: 13
ggagccgccg ccgccagaac caccaccacc agaaccacca ccacctgagg agacggtgac    60
cgtggtccc                                                             69

<210> SEQ ID NO 14
<211> LENGTH: 53
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 14
ggcggcggcg gctccggtgg tggtggatcc gaaattgtcc tcacccagtc tcc            53
```